(12) United States Patent
Hofmann et al.

(10) Patent No.: US 12,317,911 B2
(45) Date of Patent: Jun. 3, 2025

(54) FLAVOR COMPOSITIONS AND SCREENING METHODS FOR IDENTIFYING THE SAME

(71) Applicant: MARS, INCORPORATED, McLean, VA (US)

(72) Inventors: Thomas Hofmann, Neufahrn (DE); Mathias Salger, Ulm (DE); Timo Stark, Kranzberg (DE)

(73) Assignee: MARS, INCORPORATED, McLean, VA (US)

( * ) Notice: Subject to any disclaimer, the term of this patent is extended or adjusted under 35 U.S.C. 154(b) by 949 days.

(21) Appl. No.: 16/982,988

(22) PCT Filed: Mar. 20, 2019

(86) PCT No.: PCT/US2019/023237
§ 371 (c)(1),
(2) Date: Sep. 21, 2020

(87) PCT Pub. No.: WO2019/183265
PCT Pub. Date: Sep. 26, 2019

(65) Prior Publication Data
US 2021/0000152 A1    Jan. 7, 2021

Related U.S. Application Data

(60) Provisional application No. 62/645,435, filed on Mar. 20, 2018.

(51) Int. Cl.
*A23L 27/22* (2016.01)
*A23G 1/44* (2006.01)
*A23L 27/00* (2016.01)
*C01D 3/04* (2006.01)

(52) U.S. Cl.
CPC ............... *A23L 27/22* (2016.08); *A23G 1/44* (2013.01); *A23L 27/82* (2016.08); *C01D 3/04* (2013.01)

(58) Field of Classification Search
CPC ...................................................... A23L 27/22
See application file for complete search history.

(56) References Cited

U.S. PATENT DOCUMENTS

| | | | |
|---|---|---|---|
| 800,448 | A | 9/1905 | Kerr |
| 1,854,353 | A | 4/1932 | Max |
| 4,597,970 | A | 7/1986 | Sharma et al. |
| 4,671,967 | A | 6/1987 | Patel et al. |

(Continued)

FOREIGN PATENT DOCUMENTS

JP      2012029616 A      2/2012

OTHER PUBLICATIONS

Cartoni, C., et al., Taste Preference for Fatty Acids is Mediated by GPR40 and GPR120, Journal of Neuroscience, Jun. 23, 2010, pp. 8376-8382, vol. 30, No. 25.

(Continued)

*Primary Examiner* — Elizabeth Gwartney
(74) *Attorney, Agent, or Firm* — Baker Botts L.L.P.

(57) ABSTRACT

The presently disclosed subject matter relates to peptides and flavor compositions that include at least one, two, three, four, five or more peptide compounds, and screening methods for identifying the same. The flavor compositions can be used to enhance or modify the taste and/or flavor of various edible compositions such as human food products and pet food products.

8 Claims, 13 Drawing Sheets

(56) References Cited

U.S. PATENT DOCUMENTS

| | | | |
|---|---|---|---|
| 4,722,845 | A | 2/1988 | Cherukuri et al. |
| 5,888,562 | A | 3/1999 | Hansen et al. |
| 6,536,599 | B1 | 3/2003 | Nielsen |
| 6,899,911 | B2 | 5/2005 | Dewis |
| 7,968,140 | B2 | 6/2011 | Kealey |
| 8,263,168 | B2 | 9/2012 | Bellody, Jr. et al. |
| 2011/0064861 | A1* | 3/2011 | Shimono .............. A23L 27/22 426/649 |
| 2014/0205729 | A1 | 7/2014 | Didzbalis et al. |

OTHER PUBLICATIONS

De Vuyst et al., The cocoa bean fermentation process: from ecosystem analysis to starter culture development, J Appl Microbiol. Jul. 2016;121(1):5-17.

Garcia et al., Chemical Studies of Yellow Tamarillo (*Solanum betaceum* Cav.) Fruit Flavor by Using a Molecular Sensory Approach, Molecules, 21(12), 1729, Dec. 2016, (11 pgs.).

Hernández-Hernández et al., Evaluation of different fermentation processes for use by small cocoa growers in mexico, Food Sci. Nutr., (5):690-695, Jan. 2016.

Katiyar et al., Drug discovery from plant sources: An integrated approach, Ayu., Jan.-Mar. 2012, 10-19, 33(1).

Mendes et al., Chewable Tablets, Pharmaceutical Dosage Forms: Tablets, vol. 1, 1989, Chapter 8, 367-418, Marcel Dekker, Inc.

Ottinger et al., Discovery and Structure Determination of a Novel Maillard-Derived Sweetness Enhancer by Application of the Comparative Taste Dilution Analysis (cTDA), J. Agric. Food Chem., Jan. 2003, 1035-1041,51(4), (Abstract Only, 2 pgs.).

Peters, Medicated Lozenges, Pharmaceutical Dosage Forms: Tablets, vol. 1, 1989, Chapter 9, 419-582, Marcel Dekker, Inc.

Salazar et al., An UPLC-ESI-MS/MS Assay Using 6-Aminoquinolyl-NHydroxysuccinimidyl Carbamate Derivatization for Targeted Amino Acid Analysis: Application to Screening of *Arabidopsis thaliana* Mutants, Metabolites, Jul. 2012, 398-428, 2.

Schindler et al., Discover of Salt Taste Enhancing Arginyl Dipeptides in Protein Digests and Fermented Fish Sauces by Means of a Sensomics Approach, J of Agr and Food Chemistry, vol. 59, No. 23, Nov. 2011, 12578-12588.

Steensels et al., Taming Wild Yeast: Potential of Conventional and Nonconventional Yeasts in Industrial Fermentations, Annu. Rev. Microbiol., Sep. 2014, 68:61-80.

Voigt et al., Biochemistry of Cocoa Fermentation, Cocoa and Coffee Fermentations, Ch. 5, CRC Press LLC, Oct. 9, 2014, p. 193-225.

Weller, A Unifying Review of Bioassay-Guided Fractionation, Effect-Directed Analysis and Related Technique, Sensors, Jul. 2012, 9181-9209, 12(7).

PCT/US2019/023237, International Search Report mailed Sep. 12, 2019, 38 pgs.

* cited by examiner

| Pro-X | Gly | Leu | Ala | Val | Phe | Ser | Met | Lys | Glu | Ile | Thr | Arg | Gln | Asn | Asp | Tyr | His | Pro | Cys | Trp |
| X-Pro | Gly | Leu | Ala | Val | Phe | Ser | Met | Lys | Glu | Ile | Thr | Arg | Gln | Asn | Asp | Tyr | His | Pro | Cys | Trp | taste modulating activity

FIG. 8

FLAVOR COMPOSITIONS AND SCREENING METHODS FOR IDENTIFYING THE SAME

CROSS-REFERENCE TO RELATED APPLICATIONS

This application is a U.S. National Stage Patent Application under 35 U.S.C. § 371 of International Patent Application No. PCT/US2019/023237, filed on Mar. 20, 2019, which claims priority to U.S. Application Ser. No. 62/645,435, filed on Mar. 20, 2018, the contents of each of which are hereby incorporated by reference in their entireties, and to each of which priority is claimed.

FIELD

The presently disclosed subject matter relates to peptides and flavor compositions and screening methods for identifying the same. The flavor compositions can be used to enhance or modify the taste and/or flavor of various edible compositions such as human food products and pet food products.

BACKGROUND

Taste profiles for edible compositions include basic tastes such as sweet, salt, bitter, sour, umami and kokumi. Chemical compounds that elicit these tastes are often referred to as tastants. It is hypothesized that tastants are sensed by taste receptors in the mouth and throat which transmit signals to the brain where the tastants and resulting taste profiles are registered. In addition to taste profiles, edible compositions are also known to have flavor profiles. Chemical compounds that contribute to flavor profiles can be aromatic compounds that are often referred to as flavorants. It is hypothesized that flavorants are sensed by receptors in the mouth, nose, and throat. While there have been recent advances in taste and flavor technologies, there remains a need for compounds that can enhance or modify the sensory experience of edible compositions by enhancing or modifying the taste, texture, and/or flavor profiles of edible compositions.

SUMMARY OF THE INVENTION

The present application is directed to flavor compositions and methods for making and modifying such compositions across a variety of food compositions. Specifically, the present application is directed to compositions comprising one, two, three, four, five or more peptides.

In certain non-limiting embodiments, the flavor composition comprises a peptide, wherein the peptide comprises: (i) proline (Pro); and (ii) a second amino acid selected from the group consisting of alanine (Ala), serine (Ser), valine (Val), arginine (Arg), lysine (Lys), glutamate (Glu), and proline (Pro), wherein the peptide imparts a salty taste, a kokumi taste or an umami taste. In certain embodiments, the flavor composition comprises a peptide selected from the group consisting of Ala-Pro, Pro-Ala, Pro-Ser, Ser-Pro, Pro-Val, Val-Pro, Arg-Pro, Pro-Lys, Lys-Pro, Pro-Glu, Pro-Pro and any combination thereof.

In certain non-limiting embodiments, the flavor composition comprises a peptide, wherein the peptide comprises: (i) pyroglutamic acid (pGlu); and (ii) a second amino acid selected from the group consisting of glutamine (Gln), glutamate (Glu), serine (Ser) and arginine (Arg), wherein the peptide imparts a salty taste or an umami taste. In certain embodiments, the flavor composition comprises a peptide selected from the group consisting of pGlu-Gln, pGlu-Glu, pGlu-Ser, pGlu-Arg and any combination thereof. In certain embodiments, the flavor composition comprises a peptide selected from the group consisting of pGlu-Glu-Glu, pGlu-Gln-Ala-Thr and combination thereof.

In certain non-limiting embodiments, the flavor composition comprises a peptide selected from the group consisting of Val-Pro-Ala, Arg-Met-Pro, Asn-Gly-Gly-Leu-Gln, Asn-Asn-Ala-Leu, Phe-Glu, Asp-Tyr-Arg, Tyr-Gly-Asp-Gly, Ser-Pro-Val, Lys-Asp-Gln-Pro, Tyr-Val and any combination thereof. In certain embodiments, the peptide is selected from the group consisting of Val-Pro-Ala, Asn-Gly-Gly-Leu-Gln and combination thereof, and wherein the peptide imparts a kokumi taste. In certain embodiments, the peptide is selected from the group consisting of Arg-Met-Pro, Asn-Asn-Ala-Leu and combination thereof, and wherein the peptide imparts a salty taste. In certain embodiments, the peptide is Phe-Glu, and wherein the peptide imparts a sour taste.

In certain embodiments, the flavor composition is prepared from a food product source, wherein the food product source is subjected to fermentation, germination, roasting, hydrolysis, fractionation, extraction, enrichment or combinations thereof. In certain embodiments, the food product source is selected from the group consisting of cacao, wheat, corn, soy and any combination thereof. In certain embodiments, the flavor composition peptide is a synthetic peptide.

In certain embodiments, the flavor composition further comprises a salt selected from the group consisting of sodium chloride and potassium chloride. In certain embodiments, the flavor composition further comprises a compound that imparts an umami taste. In certain embodiments, the compound is monosodium glutamate.

In certain non-limiting embodiments, the presently disclosed subject matter provides a food product comprising any flavor composition disclosed herein. In certain embodiments, the peptide comprised in the flavor composition is present at a concentration of from about 0.0000001 to about 1.0% weight/weight of the food product. In certain embodiments, the peptide comprised in the flavor composition is present at a concentration of from about 0.1 to about 1000 ppb of the food product. In certain embodiments, the peptide comprised in the flavor composition is present at a concentration of from about 0.1 to about 100 ppb of the food product. In certain embodiments, the peptide comprised in the flavor composition is present at a concentration of from about 0.1 to about 100 ppt of the food product.

In certain non-limiting embodiments, the presently disclosed subject matter provides a method of increasing a saltiness intensity in a food product comprising admixing the food product with the flavor composition disclosed herein. In certain embodiments, the flavor composition peptide is present at a concentration of from about 0.0000001 to about 1.0% in the admixture. In certain embodiments, the increase in saltiness intensity comprises an increase in saltiness aftertaste.

In certain non-limiting embodiments, the presently disclosed subject matter provides a method of increasing a saltiness intensity in a food product comprising admixing the food product with the flavor composition disclosed herein. In certain embodiments, the flavor composition peptide is present at a concentration of from about 0.1 to about 1000 ppb in the admixture. In certain embodiments, the flavor composition peptide is present at a concentration of from about 0.1 to about 100 ppb in the admixture. In certain embodiments, the increase in saltiness intensity comprises an increase in saltiness aftertaste. In certain embodiments, the flavor composition peptide is present at a concentration of from about 0.1 to about 100 ppb. In certain embodiments, the flavor composition peptide is present at a concentration selected from the group consisting of about 0.1 ppb, about 0.5 ppb, about 1 ppb, about 10 ppb, about 40 ppb, about 50 ppb and about 100 ppb. In certain embodiments, the flavor composition peptide is a Pro-Val, Val-Pro, Arg-Pro, Pro-Lys or Lys-Pro peptide. In certain embodiments, the flavor composition peptide is a pGlu-Glu, pGlu-Glu-Glu or pGlu-Gln-Ala-Thr peptide. In certain embodiments, the flavor composition peptide is a Arg-Met-Pro or Asn-Asn-Ala-Leu peptide.

In certain non-limiting embodiments, the presently disclosed subject matter provides a method of reducing the amount of sodium chloride in a food product comprising admixing the food product with the flavor composition disclosed herein. In certain embodiments, the flavor composition peptide is present at a concentration of from about 0.1 to about 1000 ppb in the admixture. In certain embodiments, the amount of sodium chloride in the food system is reduced by at least 10%.

In certain non-limiting embodiments, the presently disclosed subject matter provides a method of increasing an umami intensity in a food product comprising admixing the food product with the flavor composition disclosed herein. In certain embodiments, the flavor composition peptide is present at a concentration of from about 0.1 to about 1000 ppt or from about 0.0000001 to about 1.0% in the admixture. In certain embodiments, the flavor composition peptide is present at a concentration of from about 0.1 to about 100 ppb in the admixture. In certain embodiments, the increase in umami intensity comprises an increase in umami aftertaste. In certain embodiments, the flavor composition peptide is present at a concentration of from about 0.1 to about 100 ppb. In certain embodiments, the flavor composition peptide is present at a concentration selected from the group consisting of about 0.1 ppb, about 0.5 ppb, about 1 ppb, about 10 ppb, about 40 ppb, about 50 ppb and about 100 ppb. In certain embodiments, the flavor composition peptide is a Pro-Glu or Pro-Pro peptide. In certain embodiments, the flavor composition peptide is a pGlu-Gln, pGlu-Ser or pGlu-Arg peptide. In certain embodiments, the flavor composition peptide is a mixture of Pro-Pro, Pro-Glu, Pro-Val, Ser-Pro and Arg-Pro peptide.

In certain non-limiting embodiments, the presently disclosed subject matter provides a method of increasing a kokumi intensity in a food product comprising admixing the food product with the flavor composition disclosed herein. In certain non-limiting embodiments, the presently disclosed subject matter provides a method of increasing a kokumi intensity in a food product comprising admixing the food product with a flavor composition comprising a pGlu-Val peptide, a pGlu-Ala peptide or combination thereof. In certain embodiments, the flavor composition peptide is present at a concentration of from about 0.1 to about 1000 ppt or from about 0.0000001 to about 1.0% in the admixture. In certain embodiments, the flavor composition peptide is present at a concentration of from about 0.1 to about 100 ppb in the admixture. In certain embodiments, the increase in kokumi intensity comprises an increase in kokumi aftertaste. In certain embodiments, the flavor composition peptide is present at a concentration of from about 0.1 to about 100 ppb. In certain embodiments, the flavor composition peptide is present at a concentration selected from the group consisting of about 0.1 ppb, about 0.5 ppb, about 1 ppb, about 10 ppb, about 40 ppb, about 50 ppb and about 100 ppb. In certain embodiments, the flavor composition peptide is a Ala-Pro, Pro-Ala, Pro-Ser or Ser-Pro peptide. In certain embodiments, the flavor composition peptide is a Val-Pro-Ala or Asn-Gly-Gly-Leu-Gln peptide. In certain embodiments, the flavor composition peptide is a mixture of Pro-Pro, Pro-Glu, Pro-Val, Ser-Pro and Arg-Pro peptide.

In certain embodiments, the flavor composition and/or the food product disclosed herein comprises a salt selected from the group consisting of sodium chloride and potassium chloride, and wherein the method further comprising reducing the concentration of salt in the food product.

In certain non-limiting embodiments, the presently disclosed subject matter provides a method of preparing the flavor composition disclosed herein, comprising synthesizing a synthetic peptide, wherein the synthetic peptide is at least 99% pure.

In certain non-limiting embodiments, the presently disclosed subject matter provides a method of preparing a flavor composition comprising any peptide disclosed herein, wherein the method comprises (i) providing a food product source, and (ii) subjecting the food product source to fractionation, extraction, or a combination thereof, to produce a composition enriched for the peptide.

In certain non-limiting embodiments, the presently disclosed subject matter provides a method of preparing a flavor composition comprising any peptide disclosed herein, wherein the method comprises (i) providing a food product source, and (ii) subjecting the food product source to hydrolysis to produce a composition enriched for the peptide.

In certain non-limiting embodiments, the presently disclosed subject matter provides a method of preparing a flavor composition comprising any peptide disclosed herein, wherein the method comprises (i) providing a food product source, and (ii) subjecting the food product source to fermentation, germination, roasting, hydrolysis, fractionation, extraction, or a combination thereof, to produce a composition enriched for the peptide.

In certain embodiments, the extraction is selected from the group consisting of ethanol extraction and liquid/solid extraction. In certain embodiments, the fractionation is solid phase fractionation.

The foregoing has outlined rather broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

BRIEF DESCRIPTION OF THE DRAWINGS

FIG. 8 depicts prolyl peptides having a positive taste modulating activity.

DETAILED DESCRIPTION

Figure 1:
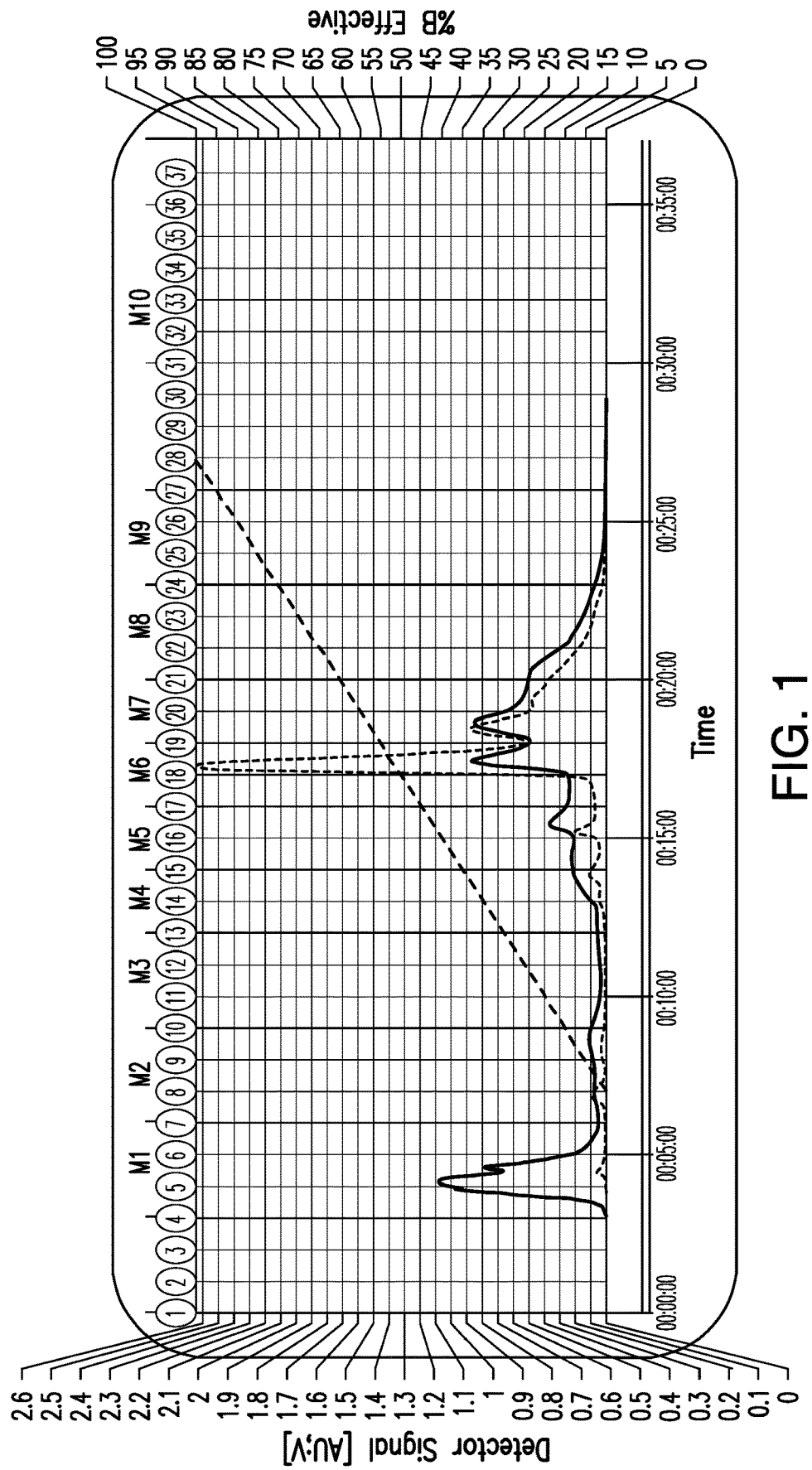
FIG. 1 depicts various fractions of the aqueous extract of 14 day beans separated by medium pressure liquid chromatography (MPLC).

To date, there remains a need for a flavor modifier that can provide a desired level of clean saltiness in various edible compositions. Additionally, there remains a need for a flavor modifier that can provide an umami taste without a salty taste, and there remains a need for a flavor modifier that can provide an umami taste at very low use levels. The present application relates to flavor compositions that include at least one, two, three, four, five or more peptide compounds. In certain non-limiting embodiments, the peptide is a dipeptide, tripeptide or combination thereof. The flavor compositions can be used to enhance or modify the taste and/or flavor of various edible compositions such as sweet goods and savory goods. The flavor compositions can include combinations of compounds, and can be added to edible compositions in various delivery system formats.

1. Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, "taste" refers to a sensation caused by activation of receptor cells in a subject's taste buds. In certain embodiments, taste can be selected from the group consisting of sweet, sour, salt, bitter, kokumi and umami. In certain embodiments, "taste" can include free fatty acid taste. See, e.g., Cartoni et al., J. of Neuroscience, 30(25): 8376-8382 (2010), the contents of which are incorporated herein by reference. In certain embodiments, a taste is elicited in a subject by a "tastant." In certain embodiments, a tastant can be a synthetic tastant. In certain embodiments, the tastant is obtained or prepared from a natural source.

As used herein, "taste profile" refers to a combination of tastes, such as, for example, one or more of a sweet, sour, salt, bitter, umami, kokumi and free fatty acid taste. In certain embodiments, a taste profile is produced by one or more tastant that is present in a composition at the same or different concentrations. In certain embodiments, a taste profile refers to the intensity of a taste or combination of tastes, for example, a sweet, sour, salt, bitter, umami, kokumi and free fatty acid taste, as detected by a subject or any assay known in the art. In certain embodiments, modifying, changing or varying the combination of tastants in a taste profile can change the sensory experience of a subject.

As used herein, "flavor" refers to one or more sensory stimuli, such as, for example, one or more of taste (gustatory), smell (olfactory), touch (tactile) and temperature (thermal) stimuli. In certain non-limiting embodiments, the sensory experience of a subject exposed to a flavor can be classified as a characteristic experience for the particular flavor. For example, a flavor can be identified by the subject as being, but not limited to, a floral, citrus, berry, nutty, caramel, chocolate, peppery, smoky, cheesy, meaty, etc., flavor.

As used herein, a flavor composition can be selected from a liquid, solution, dry powder, spray, paste, suspension and any combination thereof. The flavor can be a natural composition, an artificial composition, a nature identical, or any combination thereof.

As used interchangeably herein, "aroma" and "smell" refer to an olfactory response to a stimulus. For example, and not by way of limitation, an aroma can be produced by aromatic substances that are perceived by the odor receptors of the olfactory system.

As used herein, "flavor profile" refers to a combination of sensory stimuli, for example, tastes, such as sweet, sour, bitter, salty, umami, kokumi and free fatty acid tastes, and/or olfactory, tactile and/or thermal stimuli. In certain embodiments, the flavor profile comprises one or more flavors which contribute to the sensory experience of a subject. In certain embodiments, modifying, changing or varying the combination of stimuli in a flavor profile can change the sensory experience of a subject.

As used herein, "texture profile" or "mouthfeel" refers to a composition's physical and chemical interaction in the mouth. The texture profile of a composition can include one or more texture, such as, for example, but not limited to, astringency, hardness, cohesiveness, viscosity, elasticity, adhesiveness, brittleness, chewiness, gumminess, moisture content, grittiness, smoothness, oiliness and greasiness. In certain embodiments, the texture profile can comprise one or more texture characteristic in the same or different intensities. In certain embodiments, the texture profile can remain constant or change during a sensory experience, for example, from initial perception of a composition on the palate, to first bite, through mastication and finally, the act of swallowing.

As used herein, "sensory experience" refers to a subject's sensory perception of a taste, taste profile, flavor, flavor profile or texture profile.

As used herein, "ppt" means parts-per-trillion and is a weight relative parameter. A part-per-trillion is a picogram per gram, such that a component that is present at 10 ppt is present at 10 picograms of the specific component per 1 gram of the aggregate mixture.

As used herein, "ppb" means parts-per-billion and is a weight relative parameter. A part-per-billion is a nanogram per gram, such that a component that is present at 10 ppb is present at 10 nanograms of the specific component per 1 gram of the aggregate mixture.

As used herein, "ppm" means parts-per-million and is a weight relative parameter. A part-per-million is a microgram per gram, such that a component that is present at 10 ppm is present at 10 micrograms of the specific component per 1 gram of the aggregate mixture.

As used herein "admixing," for example, "admixing the peptide flavor composition, dipeptide flavor composition, tripeptide flavor composition, or combinations thereof of the present application with a food product," refers to the process where the flavor composition is mixed with or added to the completed product or mixed with some or all of the components of the product during product formation or some combination of these steps. When used in the context of admixing the term "product" refers to the product or any of its components. This admixing step can include a process selected from the step of adding the flavor composition to the product, spraying the flavor composition on the product, coating the flavor composition on the product, suspending the product in the flavor composition, painting the flavor composition on the product, pasting the flavor composition on the product, encapsulating the product with the flavor composition, mixing the flavor composition with the product and any combination thereof. The flavor composition can be a liquid, dry powder, spray, paste, suspension and any combination thereof.

As used herein "food product" refers to an ingestible product, such as, but not limited to, human food, animal (pet) foods, and pharmaceutical compositions.

As used herein "flavor composition" refers to at least one, two, three, four, five, or more compounds or biologically acceptable salts thereof that modulate, including enhancing, multiplying, potentiating, decreasing, suppressing, or inducing, the tastes, smells and/or flavors of a natural or synthetic tastant, flavoring agent, taste profile, flavor profile and/or texture profile in an animal or a human. In certain embodiments, the flavor composition comprises a combination of compounds or biologically acceptable salts thereof. In certain embodiments, the flavor composition includes one or more excipients.

As used herein "savory flavor" refers to a savory, "mouthwatering," sensation. In certain embodiments, a savory flavor is induced by one or more combination of umami tastants, for example, MSG (monosodium glutamate) in an animal or a human.

In certain embodiments, "wet soup category" means wet/liquid soups regardless of concentration or container, including frozen soups. For the purpose of this definition "soup(s)" means a food prepared from meat, poultry, fish, vegetables, grains, fruit and/or other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

As used herein, "dehydrated and culinary food category" means: (i) cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) meal solution products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

As used herein, "beverage category" means beverages, beverage mixes and concentrates, including but not limited to, alcoholic and non-alcoholic ready to drink and dry powdered beverages. Other examples of foods and beverages wherein compounds according to the application may be incorporated included by way of example carbonated and non-carbonated beverages, e.g., sodas, fruit or vegetable juices, alcoholic and non-alcoholic beverages, confectionary products, e.g., salad dressings, and other condiments, cereal, and other breakfast foods, canned fruits and fruit sauces and the like.

As used herein, "frozen food category" means chilled or frozen food products. Non-limiting examples of food products of the frozen food category include ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, frozen ready meals, frozen pizza, chilled pizza, frozen soup, frozen pasta, frozen processed red meat, frozen processed poultry, frozen processed fish/seafood, frozen vegetables, frozen processed vegetables, frozen meat substitutes, frozen potatoes, frozen bakery products and frozen desserts.

As used herein, "snack food category" generally refers to any food that can be a light informal meal including, but not limited to sweet and savory snacks and snack bars. Examples of snack foods include, but are not limited to, fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

As used herein, "meat food product" refers generally to a food product made by processing the edible remains of any dead animal, including birds, fish, crustaceans, shellfish and mammals. Meat food products include, without limitation, for example, prepared beef, lamb, pork, poultry or seafood products. For example, meat food products include bologna, frankfurters, sausage, luncheon, deli slices, loaves, bacon, meatballs, fish sticks, chicken fingers, and ground meats, e.g., meatloaf, meatballs and hamburgers.

As used herein, "simulated meat food product" includes, without limitation, for example, a meat alternative, meat analog, soy burger, soy bologna, soy frankfurter, soy sausage, soy luncheon loaves, soy bacon and soy meatball.

As used herein, "food product source" refers generally to the raw products from which a food product is made. In certain embodiments, the food product source is a vegetable, fruit or any other plant material. In certain embodiments, the plant material is cacao, cocoa beans, or cocoa liquor. In other embodiments, the food product source comprises the remains of any dead animal, including birds, fish, crustaceans, shellfish and mammals.

2. Fermentation Methods

In certain embodiments, processing of coca beans for generating cocoa flavor includes two steps: a fermentation step, which includes air-drying of the fermented material, and a roasting step. In certain embodiments, during fermentation the pulp surrounding the beans is degraded by microorganisms and the sugars contained in the pulp are mainly transformed to acids. In certain embodiments, in the course of the fermentative process these acids slowly diffuse into the bean resulting in an acidification of the cellular material. In certain embodiments, peptides of different sizes are generated as well as high levels of hydrophobic free amino acids, which are mainly attributed to the activity of specific proteinases. In certain embodiments, the mixture of peptides and hydrophobic amino acids are the cocoa-specific flavor precursors. Various methods of fermentation can be found in Steensels, et al., Annu Rev Microbiol. 2014; 68:61-80; De Vuyst, et al., J Appl Microbiol. 2016 July; 121(1):5-17; Hernández-Hernández, et al., Food Sci Nutr. 2016 Jan. 22; 4(5):690-5; U.S. 800,448; U.S. Pat. Nos. 5,888,562; and 1,854,353, the contents of which are incorporated herein by reference.

In certain embodiments, four major proteins with a molecular weight of 14.5, 21, 31 and 47 kDa have been identified before fermentation in cocoa beans. In certain embodiments, these proteins form to the peptide/amino acid mixture that brings the cocoa flavor.

In certain embodiments, cocoa beans are underfermented or insufficiently fermented, where the beans are fermented for about 1 to 4 days and then dried. In certain embodiments, the proteins of 21 kD and 31 kD/47 kD are largely present. In certain embodiments, the processed beans do not have a sufficient quantity of amino acids and peptides to form a cocoa flavor during subsequent roasting.

In certain embodiments, cocoa beans are well fermented, where the beans are fermented and dried for about 2 to 10 days. In certain embodiments, the protein of 21 kD is largely present, whereas the 31 kD/47 kD proteins are partially or completely degraded. In certain embodiments, the processed beans have a sufficient quantity of amino acids and peptides to form a cocoa flavor during subsequent roasting.

In certain embodiments, cocoa beans are overfermented, where the beans fermented and dried traditionally for about 7 to 15 days. In certain embodiments, the proteins of 21 kD and 31 kD/47 kD are generally degraded. In certain embodiments, the processed beans have a sufficient quantity of amino acids, but an insufficient quantity of peptide to form a cocoa flavor during subsequent roasting.

3. Screening Methods

Less than a tenth of the many thousands of chemical compositions that are found in natural products are responsible for aroma, taste and mouthfeel. State of the art separation, isolation and chemical analysis techniques have allowed the identification and quantification of key flavor compounds out of the many hundreds that may be detected in a natural product. This approach, termed "sensomics," involves trained human subjects with modern instrumental techniques, enabling the identification of the most important aroma and taste compounds from a food. It has been used extensively for food products, such as teas and wines, and can be used to analyze the flavor compounds in overfermented cocoa beans.

Various modern analytical techniques can be employed for separation, isolation and chemical structure analysis. In certain embodiments, separation techniques used to separate a flavor compound include, but are not limited to, gas chromatography (GC), liquid chromatography (LC), high performance liquid chromatography (HPLC), ultra high performance liquid chromatography (UPLC or UHPLC,) and combinations thereof. In certain embodiments, structure analysis techniques include, but are not limited to, mass spectrometry (MS), time-of-flight mass spectrometry (TOF-MS), electrospray ionization mass spectrometry (ESI-MS), mass spectrometry with low/high collision energy switching ($MS^e$), tandem mass spectrometry (MS/MS), optionally coupled with selected reaction monitoring (SRM), multiple reaction monitoring (MRM), or parallel reaction monitoring (PRM).

In certain embodiments, mass spectrometry with low/high collision energy switching ($MS^e$) is used to identify a flavor compound. In $MS^e$, the chemical compositions reaching the mass source after fractionation are subjected to ionization in low- and high-energy collision modes alternating at medium frequency, whereby complex mix of compounds can be analyzed in a single run. In certain embodiments, Electrospray ionization (ESI) is used to identify a flavor compound. ESI is a technique used in mass spectrometry to produce ions using an electrospray in which a high voltage is applied to a liquid to create an aerosol. Mass spectrometry using ESI is termed electrospray ionization mass spectrometry (ESI-MS).

In certain embodiments, the various analytical techniques can be combined to reach desired analytical outcomes. In certain embodiments, gas chromatography is combined with mass spectrometry (GC-MS). In certain embodiments, high-performance liquid chromatography is combined with tandem mass spectrometry (LC-MS/MS). In certain embodiments, UPLC is combined with ESI-MS/MS using MRM (UPLC-ESI-MS/$MS_{MRM}$). In certain embodiment, UPLC is combined with TOF-ESI-$MS^e$ (UPLC-TOF-ESI-$MS^e$).

In certain embodiments, activity-guided fractionation is used to identify a flavor compound. Activity-guided fractionation is a common approach for studying chemical compositions that are found in natural products. With this technique, fractions are screened in pursuit of those that contain biologically or chemically active compounds. The active fractions are then identified and further isolated and purified. Examples and protocols of activity-guided fractionation can be found in Garcia, et al., Molecules 2016, 21(12), 1729; Weller, Sensors (Basel) 2012; 12(7): 9181-9209; and Katiyar, et al., Ayu 2012 January; 33(1):10-9; Salazar, et al., Metabolites 2012, 2, 398-428, the contents of which are incorporated herein by reference.

In certain embodiments, comparative taste dilution analysis (cTDA) is used to identify a flavor compound. cTDA is a screening protocol for identifying taste-modifying compounds from mixtures. Examples and protocols of cTDA can be found in Ottinger, et al., J Agric Food Chem. 2003 Feb. 12; 51(4):1035-41, the contents of which are incorporated herein by reference.

In certain embodiments, activity-guided fractionation is used to separate and identify different fragments of taste compounds isolated from overfermented cocoa beans. In certain embodiments, comparative taste dilution analysis is used to identify fragments of taste compounds isolated from overfermented cocoa beans. In certain embodiments, activity-guided fractionation is combined with comparative taste dilution analysis to identify different fragments of taste compounds isolated from overfermented cocoa beans. In certain embodiments, the structures of the isolated compounds are further determined by LC-MS/MS, UPLC-ESI-MS/MS$_{MRM}$, and/or UPLC-TOF-ESI-MS$^e$.

4. Peptide Compounds

The presently disclosed subject matter relates to flavor compositions that include at least one, two, three, four, five or more peptide compounds. In certain non-limiting embodiments, the peptide is a dipeptide, a tripeptide, or combinations thereof. The flavor compositions can be used to enhance or modify the taste or flavor of various edible compositions such as human food products and pet food products. The flavor compositions can include combinations of compounds, and can be added to edible compositions in various delivery system formats.

In certain embodiments of the presently disclosed subject matter, the flavor composition comprises a dipeptide comprising a pyroglutamic acid residue (pGlu) and a second amino acid residue. In certain embodiments, the second amino acid is a hydrophobic amino acid residue. In certain embodiments, the hydrophobic amino acid is selected from the group consisting of alanine (Ala), valine (Val), leucine (Leu), isoleucine (Ile), proline (Pro), phenylalanine (Phe), methionine (Met), and tryptophan (Trp). In certain embodiments, the second amino acid residue is selected from the group consisting of alanine (Ala), arginine (Arg), asparagine (Asn), aspartic acid (aspartate, Asp), cysteine (Cys), glutamine (Gin), glutamic acid (glutamate, Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val).

In certain embodiments, the dipeptide flavor composition comprises pGlu-Val. In certain embodiments, the dipeptide flavor composition comprises pGlu-Ala. In certain embodiments, the dipeptide flavor composition comprises pGlu-Gln. In certain embodiments, the dipeptide flavor composition comprises pGlu-Phe. In certain embodiments, the dipeptide flavor composition comprises pGlu-Glu. In certain embodiments, the dipeptide flavor composition comprises pGlu-Ser. In certain embodiments, the dipeptide flavor composition comprises pau-Pro. In certain embodiments, the dipeptide flavor composition comprises pGlu-Arg.

In certain embodiments of the presently disclosed subject matter, the flavor composition comprises a dipeptide comprising a proline residue (Pro) and a second amino acid residue. In certain embodiments, the second amino acid is a hydrophobic amino acid residue. In certain embodiments, the hydrophobic amino acid is selected from the group consisting of alanine (Ala), valine (Val), leucine (Leu), isoleucine (Ile), proline (Pro), phenylalanine (Phe), methionine (Met), and tryptophan (Trp). In certain embodiments, the second amino acid residue is selected from the group consisting of alanine (Ala), arginine (Arg), asparagine (Asn), aspartic acid (aspartate, Asp), cysteine (Cys), glutamine (Gin), glutamic acid (glutamate, Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val).

In certain embodiments, the dipeptide flavor composition comprises Pro-Ala. In certain embodiments, the dipeptide flavor composition comprises Ala-Pro. In certain embodiments, the dipeptide flavor composition comprises Pro-Ser. In certain embodiments, the dipeptide flavor composition comprises Ser-Pro. In certain embodiments, the dipeptide flavor composition comprises Pro-Val. In certain embodiments, the dipeptide flavor composition comprises Val-Pro. In certain embodiments, the dipeptide flavor composition comprises Arg-Pro. In certain embodiments, the dipeptide flavor composition comprises Pro-Lys. In certain embodiments, the dipeptide flavor composition comprises Lys-Pro. In certain embodiments, the dipeptide flavor composition comprises Pro-Glu. In certain embodiments, the dipeptide flavor composition comprises Pro-Pro.

In certain embodiments of the presently disclosed subject matter, the flavor composition comprises a peptide comprising one, two, three, four, five or more amino acids each independently selected from the group consisting of glycine (Gly), alanine (Ala), valine (Val), leucine (Leu), isoleucine (Ile), proline (Pro), arginine (Arg), asparagine (Asn), aspartic acid (aspartate, Asp), cysteine (Cys), glutamine (Gln), glutamic acid (glutamate, Glu), histidine (His), lysine (Lys), methionine (Met), phenylalanine (Phe), serine (Ser), threonine (Thr), tryptophan (Trp) and tyrosine (Tyr).

In certain embodiments of the presently disclosed subject matter, the peptide flavor composition is selected from the group consisting of pEEE (pGlu-Glu-Glu), pEQAT (pGlu-Gln-Ala-Thr), VPA (Val-Pro-Ala), RMP (Arg-Met-Pro), NGGLQ (Asn-Gly-Gly-Leu-Gln), NNAL (Asn-Asn-Ala-Leu), FE (Phe-Glu), DYR (Asp-Tyr-Arg), YGDG (Tyr-Gly-Asp-Gly), SPV (Ser-Pro-Val), KDQP (Lys-Asp-Gln-Pro), YV (Tyr-Val) and combinations thereof.

In certain embodiments, the peptide flavor composition comprises a mixture two or more peptide disclosed herein. In certain embodiments, the peptide flavor composition comprises a mixture of Pro-Pro, Pro-Glu, Pro-Val, Ser-Pro and Arg-Pro. In certain embodiments, the mixture can impart a more intense taste, e.g., an umami taste and/or a kokumi taste. In certain embodiments, the threshold concentration of the mixture is lower compared to any single dipeptides therein.

In certain embodiments, the peptide compounds of the presently disclosed subject matter comprise a salt of the peptide, for example, but not limited to, an acetate salt, a TFA salt, or a formate salt. In certain embodiments, the peptide salt comprises an anion (−) (for example, but not limited to, $Cl^-$, $F^-$, $Br^-$, $O_2^-$, $CO_3^{2-}$, $HCO_3^-$, $OH^-$, $NO_3^-$, $PO_4^{3-}$, $SO_4^{2-}$, $CH_3COO^-$, $HCOO^-$, $C_2O_4^{2-}$ and $CN^-$) bonded via an ionic bond with a cation (+) (for example, but not limited to, $Al^{3+}$, $Ca^{2+}$, $Na^+$, $K^+$, $Cu^{2+}$, $H^+$, $Fe^{3+}$, $Mg^{2+}$, $Ag^+$, $NH_4^+$, $H_3O^+$, $Hg_2^{2+}$). In other embodiments, the peptide salt comprises a cation (+) bonded via an ionic bond with an anion (−).

In certain embodiments, the ionic species of the peptide salt act in conjunction with other ionic tastants to modify a sensory impression of said tastants. For example, in some embodiments, the peptide compound is combined with NaCl and/or KCl to provide a salty taste impression that has a higher level of intensity than a composition comprising NaCl and/or KCl in the absence of the peptide.

In certain embodiments, the peptide compound can be combined with a salt or salt mixture. The salt or salt mixture can comprise inorganic, organic, monoatomic as well as polyatomic ions. In certain embodiments, the salts are nontoxic and edible. In certain embodiments, the salt or salt mixtures are inorganic salts, for example, inorganic salts comprising halogen anions or phosphate ions, alkali or earth alkali metal salts. In certain embodiments, the salts are cationic salts such as, but not limited to, NaCl, KCl and $Na_3PO_4$. In certain embodiments, the salts are anionic salts such as, but not limited to acetate salt, TFA salt, and formate salt.

5. Flavor Compositions

The flavor compositions of the presently disclosed subject matter can be used to enhance or modify the sensory experience of various edible compositions such as human food products or pet food products. The flavor compositions can include combinations of compounds, and can be added to edible compositions in various food products.

In certain embodiments, the presently disclosed subject matter relates to methods for modulating the flavor of an edible product comprising: a) providing at least one comestible food product, or a precursor thereof, and b) combining the comestible food product or precursor thereof with at least a salty, umami, kokumi, bitter, astringent, flinty/mineral, sweet, sour, metallic, numbing, savory and/or free fatty acid flavor modulating amount of at least one, two, three, four, five or more flavor composition(s), or any of its subgenuses, for example, one, two three, four, five or more peptide compounds, such as a dipeptide compound(s) and/or a tripeptide compound(s), or a comestibly acceptable salt thereof, so as to form a modified edible food product.

In certain embodiments, the flavor compositions of the presently disclosed subject matter can enhance the salty taste, umami taste, bitter taste, sweet taste, sour taste, kokumi flavor, flinty/mineral flavor, metallic flavor, numbing mouthfeel, astringent mouthfeel, savory and/or free fatty acid flavor of a food product, such as, for example, an edible composition including pet foods, pharmaceutical compositions and human foods, such as soup, a confection, and/or a snack food. In certain embodiments, the flavor compositions of the presently disclosed subject matter can be used to modify, enhance or decrease the salty taste, umami taste, bitter taste, sweet taste, sour taste, kokumi flavor, flinty/mineral flavor, metallic flavor, numbing mouthfeel, astringent mouthfeel, savory and/or free fatty acid flavor of one or more of the following subgenuses of comestible compositions: confectioneries, bakery products, ice creams, dairy products, savory snacks, snack bars, meal replacement products, ready meals, soups, pastas, noodles, canned foods, frozen foods, dried foods, chilled foods, oils and fats, baby foods, or spreads, or a mixture thereof.

In certain embodiments of the application, an edible composition can be produced that contains a sufficient amount of at least one, two, three, four, five or more flavor composition(s), or its various subgenuses described herein, for example a peptide compound(s), such as a dipeptide compound(s) and/or a tripeptide compound(s), to produce a composition having the desired flavor, taste and/or mouthfeel characteristics such as "salty" and/or "umami" and/or "kokumi" and/or "savory" and/or "bitter" and/or "sweet" and/or "sour" and/or "flinty/mineral" and/or "metallic" and/or "numbing" and/or "astringent" and/or "free fatty acid" characteristic.

In certain embodiments, at least a taste and/or flavor and/or mouthfeel modulating amount of one, two, three, four, five or more of the flavor compositions of the present application can be added to the edible food product, so that the taste and/or flavor and/or mouthfeel, for example, salty taste, umami taste, kokumi taste and/or savory flavor, modified edible food product has an increased or decreased taste and/or flavor and/or mouthfeel, for example, salty taste, umami taste, kokumi taste and/or savory flavor, as compared to the edible food product prepared without the flavor composition, as determined by human beings or animals in general, or in the case of formulation testing, as determined by a taste panel of at least one, two, three, four, five or more human taste testers, via procedures known in the art.

In certain embodiments of the present application, the flavor composition is added to a food product in an amount effective to provide a clean salty taste. In certain embodiments of the present application, the flavor composition is added to a food product in an amount effective to enhance a clean salty taste. In certain embodiments, the salty taste is not associated with an umami taste. In certain embodiments of the present application, the flavor composition is added to a food product in an amount effective to increase a saltiness aftertaste.

In certain embodiments of the present application, the flavor composition is admixed with a food product comprising a salt, for example, sodium chloride and/or potassium chloride, wherein the flavor composition is admixed in an amount effective to provide a clean salty taste while reducing the concentration of salt in the food product. In certain embodiments, the concentration of salt in the food product is reduced by between about 1 and about 99%, between about 10 and about 90%, between about 20 and about 80%, between about 30 and about 70%, between about 40 and about 60%, or about 50% compared to a food product that has not been admixed with the flavor composition.

In certain embodiments of the application, an edible composition can be produced that contains a sufficient amount of at least one, two, three, four, five or more flavor composition(s), or its various subgenuses described herein, for example a peptide compound(s), such as a dipeptide compound(s) and/or a tripeptide compound(s), to produce a composition having the desired flavor or taste characteristics such as an "umami" taste.

In certain embodiments, at least an umami taste modulating amount of one, two, three, four, five or more of the flavor compositions of the present application can be added to the edible food product, so that the umami taste modified edible food product has an increased or decreased umami taste as compared to the edible food product prepared without the flavor composition, as determined by human beings or animals in general, or in the case of formulation testing, as determined by a taste panel of at least one, two, three, four, five or more human taste testers, via procedures known in the art.

In certain embodiments of the present application, the flavor composition is added to a food product in an amount effective to provide an umami taste.

In certain embodiments of the application, an edible composition can be produced that contains a sufficient amount of at least one, two, three, four, five or more flavor composition(s), or its various subgenuses described herein, for example a peptide compound(s), such as a dipeptide compound(s) and/or a tripeptide compound(s), to produce a composition having the desired flavor or taste characteristics such as a "bitter" taste.

In certain embodiments, at least a bitter taste modulating amount of one, two, three, four, five or more of the flavor compositions of the present application can be added to the edible food product, so that the bitter taste modified edible food product has an increased or decreased bitter taste as compared to the edible food product prepared without the flavor composition, as determined by human beings or animals in general, or in the case of formulation testing, as determined by a taste panel of at least one, two, three, four, five or more human taste testers, via procedures known in the art.

In certain embodiments of the present application, the flavor composition is added to a food product in an amount effective to provide a bitter taste.

In certain embodiments of the application, an edible composition can be produced that contains a sufficient amount of at least one, two, three, four, five or more flavor composition(s), or its various subgenuses described herein, for example a peptide compound(s), such as a dipeptide compound(s) and/or a tripeptide compound(s), to produce a composition having the desired flavor or taste characteristics such as a "sweet" taste.

In certain embodiments, at least a sweet taste modulating amount of one, two, three, four, five or more of the flavor compositions of the present application can be added to the edible food product, so that the sweet taste modified edible food product has an increased or decreased sweet taste as compared to the edible food product prepared without the flavor composition, as determined by human beings or animals in general, or in the case of formulation testing, as determined by a taste panel of at least one, two, three, four, five or more human taste testers, via procedures known in the art.

In certain embodiments of the present application, the flavor composition is added to a food product in an amount effective to provide a sweet taste.

In certain embodiments of the application, an edible composition can be produced that contains a sufficient amount of at least one, two, three, four, five or more flavor composition(s), or its various subgenuses described herein, for example a peptide compound(s), such as a dipeptide compound(s) and/or a tripeptide compound(s), to produce a composition having the desired flavor or taste characteristics such as a "sour" taste.

In certain embodiments, at least a sour taste modulating amount of one, two, three, four, five or more of the flavor compositions of the present application can be added to the edible food product, so that the sour taste modified edible food product has an increased or decreased sour taste as compared to the edible food product prepared without the flavor composition, as determined by human beings or animals in general, or in the case of formulation testing, as determined by a taste panel of at least one, two, three, four, five or more human taste testers, via procedures known in the art.

In certain embodiments of the present application, the flavor composition is added to a food product in an amount effective to provide a sour taste.

In certain embodiments of the application, an edible composition can be produced that contains a sufficient amount of at least one, two, three, four, five or more flavor composition(s), or its various subgenuses described herein, for example a peptide compound(s), such as a dipeptide compound(s) and/or a tripeptide compound(s), to produce a composition having the desired flavor or taste characteristics such as a "kokumi" flavor.

In certain embodiments, at least an umami taste modulating amount of one, two, three, four, five or more of the flavor compositions of the present application can be added to the edible food product, so that the kokumi flavor modified edible food product has an increased or decreased kokumi flavor as compared to the edible food product prepared without the flavor composition, as determined by human beings or animals in general, or in the case of formulation testing, as determined by a taste panel of at least one, two, three, four, five or more human taste testers, via procedures known in the art.

In certain embodiments of the present application, the flavor composition is added to a food product in an amount effective to provide a kokumi flavor.

In certain embodiments of the application, an edible composition can be produced that contains a sufficient amount of at least one, two, three, four, five or more flavor composition(s), or its various subgenuses described herein, for example a peptide compound, such as a dipeptide compound(s) and/or a tripeptide compound(s), to produce a composition having the desired flavor or taste characteristics such as a "savory" flavor.

In certain embodiments, at least a savory flavor modulating amount of one, two, three, four, five or more of the flavor compositions of the present application can be added to the edible food product, so that the savory flavor modified edible food product has an increased or decreased savory flavor as compared to the edible food product prepared without the flavor composition, as determined by human beings or animals in general, or in the case of formulation testing, as determined by a taste panel of at least one, two, three, four, five or more human taste testers, via procedures known in the art.

In certain embodiments of the present application, the flavor composition is added to a food product in an amount effective to provide a savory flavor.

In certain embodiments of the application, an edible composition can be produced that contains a sufficient amount of at least one, two, three, four, five or more flavor composition(s), or its various subgenuses described herein, for example a peptide compound(s), such as a dipeptide compound(s) and/or a tripeptide compound(s), to produce a composition having the desired flavor or taste characteristics such as a "flinty/mineral" flavor.

In certain embodiments, at least a flinty/mineral flavor modulating amount of one, two, three, four, five or more of the flavor compositions of the present application can be added to the edible food product, so that the flinty/mineral flavor modified edible food product has an increased or decreased flinty/mineral flavor as compared to the edible food product prepared without the flavor composition, as determined by human beings or animals in general, or in the case of formulation testing, as determined by a taste panel of at least one, two, three, four, five or more human taste testers, via procedures known in the art.

In certain embodiments of the present application, the flavor composition is added to a food product in an amount effective to provide a flinty/mineral flavor.

In certain embodiments of the application, an edible composition can be produced that contains a sufficient amount of at least one, two, three, four, five or more flavor composition(s), or its various subgenuses described herein, for example a peptide compound(s), such as a dipeptide compound(s) and/or a tripeptide compound(s), to produce a composition having the desired flavor or taste characteristics such as a "metallic" flavor.

In certain embodiments, at least a metallic flavor modulating amount of one, two, three, four, five or more of the flavor compositions of the present application can be added to the edible food product, so that the metallic flavor modified edible food product has an increased or decreased metallic flavor as compared to the edible food product prepared without the flavor composition, as determined by human beings or animals in general, or in the case of formulation testing, as determined by a taste panel of at least one, two, three, four, five or more human taste testers, via procedures known in the art.

In certain embodiments of the present application, the flavor composition is added to a food product in an amount effective to provide a metallic flavor.

In certain embodiments, the peptide compounds of the present application provide a sour taste to a chocolate confection. In certain embodiments, the peptide compounds are admixed with a chocolate confectionary to provide an acetic acid sourness characteristic to the chocolate confectionery. In certain embodiments, the acetic acid sourness is an acetic acid sourness characteristic associated with chocolate confectionery products made from fully fermented cocoa beans sourced from West Africa.

In certain embodiments, adding peptide compounds of the present application to chocolate confectionery products made from cacao and/or cocoa beans that have been sourced from West Africa but under-fermented, or from cacao and/or cocoa beans that have been sourced from other geographies, provides the same taste and flavor profiles as chocolate confectionery made from fully fermented West African cocoa beans.

In certain embodiments, the flavor composition, or any of its subgenuses, for example, a peptide compound, such as a dipeptide compound and/or a tripeptide compound, or a comestibly acceptable salt thereof, of the present application, can be combined with an edible composition in an amount effective to modify, enhance or otherwise alter a taste or taste profile of the edible composition. The modification can include, for example, an increase or decrease in one or more of a sweet, sour, salty, bitter, kokumi and/or umami taste of the composition.

In certain embodiments, the flavor composition, or any of its subgenuses, for example, a peptide compound, such as a dipeptide compound and/or a tripeptide compound, or a comestibly acceptable salt thereof, of the present application, can be combined with an edible composition in an amount effective to modify, enhance or otherwise alter a flavor or flavor profile of the edible composition. The modification can include, for example, an increase or decrease in the perception of one or more sensory stimuli, such as, for example, one or more of taste (gustatory), smell (olfactory), touch (tactile) and temperature (thermal).

In certain embodiments, the flavor composition, or any of its subgenuses, for example, a peptide compound, such as a dipeptide compound and/or a tripeptide compound, or a comestibly acceptable salt thereof, of the present application, can be combined with an edible composition in an amount effective to modify, enhance or otherwise alter a texture profile of the edible composition. The texture benefit can include, for example, an increased clean mouthfeel sensory attribute. In certain embodiments, admixing the peptide compounds of the present application with a chocolate confectionary reduces a fatty mouthcoating texture.

In certain embodiments of the application, an edible composition can be produced that contains a sufficient amount of at least one, two, three, four, five or more flavor composition(s), or its various subgenuses described herein, for example a peptide compound(s), such as a dipeptide compound(s) and/or a tripeptide compound(s), to produce a composition having the desired flavor or taste characteristics such as an "astringent" mouthfeel.

In certain embodiments, at least an astringent mouthfeel modulating amount of one, two, three, four, five or more of the flavor compositions of the present application can be added to the edible food product, so that the astringent mouthfeel modified edible food product has an increased or decreased astringent mouthfeel as compared to the edible food product prepared without the flavor composition, as determined by human beings or animals in general, or in the case of formulation testing, as determined by a taste panel of at least one, two, three, four, five or more human taste testers, via procedures known in the art.

In certain embodiments of the present application, the flavor composition is added to a food product in an amount effective to provide an astringent mouthfeel.

In certain embodiments of the application, an edible composition can be produced that contains a sufficient amount of at least one, two, three, four, five or more flavor composition, or its various subgenuses described herein, for example a peptide compound(s), such as a dipeptide compound(s) and/or a tripeptide compound(s), to produce a composition having the desired flavor or taste characteristics such as an "numbing" mouthfeel.

In certain embodiments, at least a numbing mouthfeel modulating amount of one, two, three, four, five or more of the flavor compositions of the present application can be added to the edible food product, so that the numbing mouthfeel modified edible food product has an increased or decreased numbing mouthfeel as compared to the edible food product prepared without the flavor composition, as determined by human beings or animals in general, or in the case of formulation testing, as determined by a taste panel of at least one, two, three, four, five or more human taste testers, via procedures known in the art.

In certain embodiments of the present application, the flavor composition is added to a food product in an amount effective to provide a numbing mouthfeel.

The concentration of flavor composition admixed with an edible food product to modulate or improve the flavor of the edible food product or composition can vary dependent on variables, such as, for example, the specific type of edible composition, what salty, umami, kokumi, savory, bitter, sweet, sour, flinty/mineral, metallic, numbing, and/or astringent compounds are already present in the edible food product and the concentrations thereof, the amount of MSG already present in the food product, and the enhancer effect of the particular flavor composition on such salty, umami, kokumi, savory, bitter, sweet, sour, flinty/mineral, metallic, numbing, and/or astringent compounds.

In certain embodiments, admixing the flavor compositions of the present application with an edible food product modulates, for example, induces, enhances or inhibits, the salty taste, umami taste, bitter taste, sweet taste, sour taste, kokumi flavor, flinty/mineral flavor, metallic flavor, numbing mouthfeel, astringent mouthfeel and/or savory flavor (or other taste or flavor properties) of other natural or synthetic salty tastants, umami tastants, bitter tastants, astringent flavorant and/or savory flavorants, for example, NaCl and/or MSG.

A broad range of concentrations of the flavor compositions can be employed to provide such salty taste, umami taste, bitter taste, astringent mouthfeel and/or savory flavor modification. In certain embodiments of the present application, the flavor composition is admixed with a food product wherein the flavor composition is present in an amount of from about 0.001 to about 500 ppt, or from about 0.005 to about 250 ppt, or from about 0.01 to about 200 ppt, or from about 0.05 to about 150 ppt, or from about 0.1 to about 100 ppt, or from about 0.5 to about 50 ppt, and values in between.

In certain embodiments, the flavor composition is admixed with a food product at a concentration of from about 0.1 to about 100 ppt, and values in between. In certain embodiments, the flavor composition is admixed with a food product at a concentration of from about 0.1 to about 50 ppt, and values in between. In certain embodiments, the flavor composition is admixed with a food product at a concentration of from about 0.1 to about 10 ppt, and values in between.

In certain embodiments, the flavor composition is admixed with a food product at a concentration of from about 0.1 to about 100 ppt, or from about 1 to about 90 ppt, or from about 10 to about 80 ppt, or from about 20 to about 70 ppt, or from about 30 to about 60 ppt, or from about 40 to about 50 ppt, and values in between.

In certain embodiments, the flavor composition is admixed with a food product at a concentration of from about 0.1 to about 1 ppt, from about 1 to about 5 ppt, from about 5 to about 10 ppt, from about 10 to about 15 ppt, from about 15 to about 20 ppt, from about 20 to about 25 ppt, from about 25 to about 30 ppt, from about 30 to about 35 ppt, from about 35 to about 40 ppt, from about 40 to about 45 ppt, from about 45 to about 50 ppt, from about 50 to about 55 ppt, from about 55 to about 60 ppt, from about 60 to about 65 ppt, from about 65 to about 70 ppt, from about 70 to about 75 ppt, from about 75 to about 80 ppt, from about 80 to about 85 ppt, from about 85 to about 90 ppt from about 90 to about 95 ppt, or from about 95 to about 100 ppt, and values in between, and values in between.

In certain embodiments of the present application, the flavor composition is admixed with a food product wherein the flavor composition is present in an amount of from about 0.001 to about 500 ppb, or from about 0.005 to about 250 ppb, or from about 0.01 to about 200 ppb, or from about 0.05 to about 150 ppb, or from about 0.1 to about 100 ppb, or from about 0.5 to about 50 ppb, and values in between.

In certain embodiments, the flavor composition is admixed with a food product at a concentration of from about 0.01 to about 10000 ppb, and values in between. In certain embodiments, the flavor composition is admixed with a food product at a concentration of from about 0.1 to about 1000 ppb, and values in between. In certain embodiments, the flavor composition is admixed with a food product at a concentration of from about 1 to about 100 ppb, and values in between. In certain embodiments, the flavor composition is admixed with a food product at a concentration of from about 10 to about 50 ppb, and values in between. In certain embodiments, the flavor composition is admixed with a food product at a concentration of from about 0.1 to about 10 ppb, and values in between.

In certain embodiments, the flavor composition is admixed with a food product at a concentration of from about 0.1 to about 10000 ppb, or from about 1 to about 5000 ppb, or from about 10 to about 2000 ppb, or from about 20 to about 1500 ppb, or from about 30 to about 1000 ppb, or from about 40 to about 500 ppb, or from about 50 to about 250 ppb, or from about 60 to about 200 ppb, or from about 70 to about 150 ppb, or from about 80 to about 100 ppb, and values in between.

In certain embodiments, the flavor composition is admixed with a food product at a concentration of from about 0.1 to about 1 ppb, from about 1 to about 5 ppb, from about 5 to about 10 ppb, from about 10 to about 15 ppb, from about 15 to about 20 ppb, from about 20 to about 25 ppb, from about 25 to about 30 ppb, from about 30 to about 35 ppb, from about 35 to about 40 ppb, from about 40 to about 45 ppb, from about 45 to about 50 ppb, from about 50 to about 55 ppb, from about 55 to about 60 ppb, from about 60 to about 65 ppb, from about 65 to about 70 ppb, from about 70 to about 75 ppb, from about 75 to about 80 ppb, from about 80 to about 85 ppb, from about 85 to about 90 ppb from about 90 to about 95 ppb, from about 95 to about 100 ppb, from about 100 to about 150 ppb, from about 150 to about 200 ppb, from about 200 to about 250 ppb, from about 250 to about 300 ppb, from about 300 to about 350 ppb, from about 350 to about 400 ppb, from about 400 to about 450 ppb, from about 450 to about 500 ppb, from about 500 to about 550 ppb, from about 550 to about 600 ppb, from about 600 to about 650 ppb, from about 650 to about 700 ppb, from about 700 to about 750 ppb, from about 750 to about 800 ppb, from about 800 to about 850 ppb, from about 850 to about 900 ppb, from about 900 to about 950 ppb, or from about 950 to about 1000 ppb, and values in between.

In certain embodiments, the flavor composition is admixed with a food product at a concentration of about 0.1 ppb, 0.5 ppb, 1 ppb, 10 ppb, 40 ppb, 50 ppb, 100 ppb, 250 ppb, 267 ppb, 1000 ppb or 1150 ppb.

In certain embodiments, the range of concentrations can include from about 1 ppb to about 100 ppb, less than 100 ppb, at least 30 ppb, and from about 30 ppb to about 1% w/w by weight of the edible composition.

In certain embodiments, the flavor composition is admixed with a food product in an amount effective to increase the salt perception of a salt reference by about 1 to about 10 fold, or from about 1.25 to about 8 fold, or from about 1.5 to about 6 fold, or from about 1.75 to about 4 fold, or from about 2 to about 2.5 fold, and values in between. In certain embodiments, the food product comprises the salt reference. In certain embodiments, the salt reference is the salt perception of the food product prior to admixing the food product with the flavor composition.

In certain embodiments of the present application, the flavor composition is admixed with a food product wherein the flavor composition is present in an amount of from between about 0.1 to about 100 ppb, and values in between.

In certain embodiments of the present application, the flavor composition is admixed with a food product wherein the flavor composition is present in an amount of from about 0.001 ppm to 100 ppm, or narrower alternative ranges from about 0.1 ppm to about 10 ppm, from about 0.01 ppm to about 30 ppm, from about 0.05 ppm to about 15 ppm, from about 0.1 ppm to about 5 ppm, or from about 0.1 ppm to about 3 ppm, and values in between.

In certain embodiments, the flavor composition is admixed with a food product at a concentration of from about 0.1 to about 100 ppm, and values in between. In certain embodiments, the flavor composition is admixed with a food product at a concentration of from about 0.1 to about 50 ppm, and values in between. In certain embodiments, the flavor composition is admixed with a food product at a concentration of from about 0.1 to about 10 ppm, and values in between.

In certain embodiments, the flavor composition is admixed with a food product at a concentration of from about 0.1 to about 100 ppm, or from about 1 to about 90 ppm, or from about 10 to about 80 ppm, or from about 20 to about 70 ppm, or from about 30 to about 60 ppm, or from about 40 to about 50 ppm, and values in between.

In certain embodiments, the flavor composition is admixed with a food product at a concentration of from about 0.1 to about 1 ppm, from about 1 to about 5 ppm, from about 5 to about 10 ppm, from about 10 to about 15 ppm, from about 15 to about 20 ppm, from about 20 to about 25 ppm, from about 25 to about 30 ppm, from about 30 to about 35 ppm, from about 35 to about 40 ppm, from about 40 to about 45 ppm, from about 45 to about 50 ppm, from about 50 to about 55 ppm, from about 55 to about 60 ppm, from about 60 to about 65 ppm, from about 65 to about 70 ppm, from about 70 to about 75 ppm, from about 75 to about 80 ppm, from about 80 to about 85 ppm, from about 85 to about 90 ppm from about 90 to about 95 ppm, or from about 95 to about 100 ppm, and values in between.

In certain embodiments, the flavor composition is admixed with a food product at a concentration of from about 0.0001 to about 99.9% weight/weight (w/w), and values in between. In certain embodiments, the flavor composition is admixed with a food product at a concentration of from about 0.0001 to about 1.0% w/w, and values in between. In certain embodiments, the flavor composition is admixed with a food product at a concentration of from about 0.0001 to about 0.5% w/w, and values in between.

In certain embodiments, the flavor composition is admixed with a food product at a concentration of from about 0.0001 to about 99.9% w/w, or from 0.001 to about 99% w/w, or from about 0.01 to about 95% w/w, or from about 0.1 to about 90% w/w, or from about 0.5 to about 85% w/w, or from about 1 to about 80% w/w, or from about 1.5 to about 75% w/w, or from about 2 to about 70% w/w, or from about 2.5 to about 65% w/w, or from about 3 to about 60% w/w, or from about 3.5 to about 55% w/w, or from about 4 to about 50% w/w, or from about 5 to about 45% w/w, or from about 10 to about 40% w/w, or from about 15 to about 35% w/w, or from about 20 to about 30% w/w, and values in between.

In certain embodiments of the present application, the flavor composition is admixed with a food product wherein the flavor composition is present in an amount of from about 0.0000001 to about 99.999% weight/weight (w/w), or from about 0.00005 to about 75% w/w, or from about 0.0001 to about 50% w/w, or from about 0.0005 to about 25% w/w, or from about 0.001 to about 10% w/w, or from about 0.005 to about 5% w/w of the food product, and values in between.

In certain embodiments, the peptide compounds of the present application are blended together in various ratios or are blended together with other compounds to form various flavor compositions. In certain embodiments, the peptide compounds that are blended are peptides, such as for example, dipeptides, tripeptides, and/or combinations thereof. In certain embodiments, the peptide compounds and other compounds are blended together, wherein each of the peptide compounds and other compounds are present in an amount of from about 0.0000001 to about 99.999% weight/ weight (w/w), or from about 0.00005 to about 75% w/w, or from about 0.0001 to about 50% w/w, or from about 0.0005 to about 25% w/w, or from about 0.001 to about 10% w/w, or from about 0.005 to about 5% w/w of the flavor composition, and values in between.

In certain embodiments, the flavor composition is admixed with a food product in an effective amount, such that a subject would be able to tell the food product apart from a food product prepared without the flavor composition, wherein the subject is a human being or animal in general, or in the case of formulation testing, as determined by a taste panel of at least one, two, three, four, five or more human taste testers, via procedures known in the art.

In certain embodiments, the flavor composition is admixed with a food product in an amount effective to increase or decrease a taste and/or flavor and/or mouthfeel in a subject that persists after the food product is no longer in contact with the mouth, tongue and/or throat of a subject. In certain embodiments, the increase or decrease persists for between about 0.5 and about 15 minutes, or between about 2 and about 13 minutes, or between about 4 and about 11 minutes, or between about 6 and about 9 minutes.

In certain embodiments, the peptides that are blended together in various ratios or are blended together with other compounds to form various flavor compositions, are peptide compounds, for example dipeptide and/or tripeptide compounds, of the present application. In certain embodiments, the flavor composition comprises one, two, three, four, five or more peptide compound(s) in combination with one or more additional compound with similar solubilities as the peptide compounds.

In certain embodiments, the flavor composition further comprises a salt selected from the group consisting of sodium chloride and potassium chloride.

In certain embodiments, the salt is admixed with the flavor composition at a concentration of from about 0.0001 to about 99.9% weight/weight (w/w), and values in between. In certain embodiments, the salt is admixed with the flavor composition at a concentration of from about 0.0001 to about 1.0% w/w, and values in between. In certain embodiments, the salt is admixed with the flavor composition at a concentration of from about 0.0001 to about 0.5% w/w, and values in between. In certain embodiments, the salt is admixed with the flavor composition at a concentration of from about 0.0001 to about 99.9% w/w, or from 0.001 to about 99% w/w, or from about 0.01 to about 95% w/w, or from about 0.1 to about 90% w/w, or from about 0.5 to about 85% w/w, or from about 1 to about 80% w/w, or from about 1.5 to about 75% w/w, or from about 2 to about 70% w/w, or from about 2.5 to about 65% w/w, or from about 3 to about 60% w/w, or from about 3.5 to about 55% w/w, or from about 4 to about 50% w/w, or from about 5 to about 45% w/w, or from about 10 to about 40% w/w, or from about 15 to about 35% w/w, or from about 20 to about 30% w/w, and values in between.

In certain embodiments of the present application, the salt is admixed with the flavor composition at an amount of from about 0.0000001 to about 99.999% weight/weight (w/w), or from about 0.00005 to about 75% w/w, or from about 0.0001 to about 50% w/w, or from about 0.0005 to about 25% w/w, or from about 0.001 to about 10% w/w, or from about 0.005 to about 5% w/w of the food product, and values in between.

In certain embodiments, the flavor composition further comprises a compound that imparts an umami taste. In certain embodiments, the compound is a prolyl peptide or a pyroglutamyl peptide. In certain embodiments, the compound is any peptide disclosed herein that imparts an umami taste. In certain embodiments, the compound is Pro-Glu, Pro-Pro, pGlu-Gln, pGlu-Ser or pGlu-Arg. In certain embodiments, the compound is monosodium glutamate.

In certain embodiments, the compound is admixed with the flavor composition at a concentration of from about 0.0001 to about 99.9% weight/weight (w/w), and values in between. In certain embodiments, the compound is admixed with the flavor composition at a concentration of from about 0.0001 to about 1.0% w/w, and values in between. In certain embodiments, the compound is admixed with the flavor composition at a concentration of from about 0.0001 to about 0.5% w/w, and values in between. In certain embodiments, the compound is admixed with the flavor composition at a concentration of from about 0.0001 to about 99.9% w/w, or from 0.001 to about 99% w/w, or from about 0.01 to about 95% w/w, or from about 0.1 to about 90% w/w, or from about 0.5 to about 85% w/w, or from about 1 to about 80% w/w, or from about 1.5 to about 75% w/w, or from about 2 to about 70% w/w, or from about 2.5 to about 65% w/w, or from about 3 to about 60% w/w, or from about 3.5 to about 55% w/w, or from about 4 to about 50% w/w, or from about 5 to about 45% w/w, or from about 10 to about 40% w/w, or from about 15 to about 35% w/w, or from about 20 to about 30% w/w, and values in between. In certain embodiments of the present application, the compound is admixed with the flavor composition at an amount of from about 0.0000001 to about 99.999% weight/weight (w/w), or from about 0.00005 to about 75% w/w, or from about 0.0001 to about 50% w/w, or from about 0.0005 to about 25% w/w, or from about 0.001 to about 10% w/w, or from about 0.005 to about 5% w/w of the food product, and values in between.

6. Delivery Systems

In certain embodiments, the flavor compositions of the present application can be incorporated into a delivery system for use in edible compositions. In certain embodiments, the composition will comprise another flavor or taste modifier such as a salty, umami, bitter, astringent and/or savory tastant. Delivery systems can be liquid or solid, aqueous or non-aqueous. Delivery systems are generally adapted to suit the needs of the flavor composition and/or the edible composition into which the flavor composition will be incorporated.

The flavoring compositions can be employed in liquid form, dried form, and/or solid form. When used in dried form, suitable drying means such as spray drying can be used. Alternatively, a flavoring composition can be encapsulated or absorbed onto water soluble materials, including but not limited to materials such as cellulose, starch, sugar, maltodextrin, gum arabic and so forth. The actual techniques for preparing such dried forms are well-known in the art, and can be applied to the presently disclosed subject matter.

The flavoring compositions of the presently disclosed subject matter can be used in many distinct physical forms well known in the art to provide an initial burst of taste, flavor and/or texture; and/or a prolonged sensation of taste, flavor and/or texture. Without being limited thereto, such physical forms include free forms, such as spray dried, powdered, and beaded forms, and encapsulated forms, and mixtures thereof.

In specific embodiments, as noted above, encapsulation techniques can be used to modify the flavor systems. In certain embodiments, flavor compounds, flavor components, or the entire flavor system can be fully or partially encapsulated. Encapsulating materials and/or techniques can be selected to determine the type of modification of the flavor system.

In specific embodiments, the encapsulating materials and/or techniques are selected to improve the stability of the flavor compounds, flavor components, or flavor systems; while in other embodiments the encapsulating materials and/or techniques are selected to modify the release profile of the flavor compounds, flavor components, or flavor systems.

Suitable encapsulating materials can include, but are not limited to, hydrocolloids such as alginates, pectins, agars, guar gums, celluloses, and the like, proteins, polyvinyl acetate, polyethylene, crosslinked polyvinyl pyrrolidone, polymethylmethacrylate, polylactidacid, polyhydroxyalkanoates, ethylcellulose, polyvinyl acetatephthalate, polyethylene glycol esters, methacrylicacid-co-methylmethacrylate, ethylene-vinylacetate (EVA) copolymer, and the like, and combinations thereof. Suitable encapsulating techniques can include, but are not limited to, spray coating, spray drying, spray chilling, absorption, adsorption, inclusion complexing (e.g., creating a flavor/cyclodextrin complex), coacervation, fluidized bed coating, or other process can be used to encapsulate an ingredient with an encapsulating material.

Encapsulated delivery systems for flavoring agents or sweetening agents contain a hydrophobic matrix of fat or wax surrounding a sweetening agent or flavoring agent core. The fats can be selected from any number of conventional materials such as fatty acids, glycerides or poly glycerol esters, sorbitol esters, and mixtures thereof. Examples of fatty acids include but are not limited to hydrogenated and partially hydrogenated vegetable oils such as palm oil, palm kernel oil, peanut oil, rapeseed oil, rice bran oil, soybean oil, cottonseed oil, sunflower oil, safflower oil, and mixtures thereof. Examples of glycerides include but are not limited to monoglycerides, diglycerides, and triglycerides.

Waxes useful can be chosen from the group consisting of natural and synthetic waxes, and mixtures thereof. Non-limiting examples include paraffin wax, petrolatum, carbowax, microcrystalline wax, beeswax, carnauba wax, candellila wax, lanolin, bayberry wax, sugarcane wax, spermaceti wax, rice bran wax, and mixtures thereof.

The fats and waxes can be use individually or in combination in amounts varying from about 10 to about 70%, and alternatively in amounts from about 30 to about 60%, by weight of the encapsulated system. When used in combination, the fat and wax are preferably present in a ratio from about 70:10 to 85:15, respectively.

Typical encapsulated flavor compositions, flavoring agent or sweetening agent delivery systems are disclosed in U.S. Pat. Nos. 4,597,970 and 4,722,845, the disclosures of which are incorporated herein by reference in their entireties.

Liquid delivery systems can include, but are not limited to, systems with a dispersion of peptide compound(s) or the flavor compositions of the present application, such as in carbohydrate syrups and/or emulsions. Liquid delivery systems can also include extracts where the peptide compound(s) and/or the flavor compositions are solubilized in a solvent. Solid delivery systems can be created by spray drying, spray coating, spray chilling, fluidized bed drying, absorption, adsorption, coacervation, complexation, or any other standard technique. In some embodiments, the delivery system can be selected to be compatible with or to function in the edible composition. In some embodiments, the delivery system will include an oleaginous material such as a fat or oil. In some embodiments, the delivery system will include a confectionery fat such as cocoa butter, a cocoa butter replacer, a cocoa butter substitute, or a cocoa butter equivalent.

When used in dried form, suitable drying means such as spray drying may be used. Alternatively, a flavoring composition may be adsorbed or absorbed onto substrates such as water soluble materials, such as cellulose, starch, sugar, maltodextrin, gum arabic and so forth or may be encapsulated. The actual techniques for preparing such dried forms are well known in the art.

7. End Product Systems

The flavoring compositions of the present disclosed subject matter can be used in a wide variety of ingestible vehicles. Non-limiting examples of suitable ingestible vehicles include chewing gum compositions, hard and soft confections, dairy products, beverage products including juice products and soft drinks, pharmaceuticals, bakery goods, frozen foods, food products and food categories described herein. The combination of the flavoring composition of the presently disclosed subject matter together with an ingestible vehicle and optional ingredients, when desired, provides a flavoring agent that possesses unexpected taste, flavor and/or texture value and imparts, for example, a salty, umami, bitter, astringent and/or savory sensory experience.

In the method for flavoring an ingestible composition of the presently disclosed subject matter, the ingestible composition is prepared by admixing the flavoring agent in an ingestible vehicle, together with any optional ingredients, to form a uniform mixture. The final compositions are readily prepared using standard methods and apparatus generally known by those skilled in the corresponding arts, such as confectionary arts. The apparatus useful in accordance with the presently disclosed subject matter comprises mixing apparatus well known in the art, and therefore the selection of the specific apparatus will be apparent to the artisan.

In certain embodiments, the present application relates to the modified edible food products produced by the methods disclosed herein. In certain embodiments, the food products can be produced by processes for producing comestible products well known to those of ordinary skill in the art, especially if such compositions comprise NaCl and/or MSG, wherein the flavor composition of the present application is employed as a salty tastant, umami tastant, bitter tastant, astringent flavorant and/or savory flavorant enhancer for the NaCl and/or MSG present in the food product.

The flavor composition and its various subgenuses can be combined with or applied to a comestible or medicinal products or precursor thereof in any of innumerable ways known to cooks the world over, or producers of comestible or medicinal products. For example, the flavor compositions can be dissolved in or dispersed in one of many known comestibly acceptable liquids, solids, or other carriers, such as water at neutral, acidic, or basic pH, fruit or vegetable juices, vinegar, marinades, beer, wine, natural water/fat emulsions such as milk or condensed milk, whey or whey products, edible oils and shortenings, fatty acids, certain low molecular weight oligomers of propylene glycol, glyceryl esters of fatty acids, and dispersions or emulsions of such hydrophobic substances in aqueous media, salts such as sodium chloride, vegetable flours, solvents such as ethanol, solid edible diluents such as vegetable powders or flours, and the like, and then combined with precursors of the comestible or medicinal products, or applied directly to the comestible or medicinal products.

In certain embodiments, the flavor compositions of the present application can be admixed with foods, beverages and other comestible compositions wherein savory compounds, especially NaCl, MSG, inosine monophosphate (IMP), or guanosine monophosphate (GMP) are conventionally utilized. These compositions include compositions for human and animal consumption, for example, food or drinks (liquids) for consumption by agricultural animals, pets and zoo animals. Those of ordinary skill in the art of preparing and selling comestible compositions (i.e., edible foods or beverages, or precursors or flavor modifiers thereof) are well aware of a large variety of classes, subclasses and species of the comestible compositions, and utilize well-known and recognized terms of art to refer to those comestible compositions while endeavoring to prepare and sell various of those comestible compositions. Such a list of terms of art is enumerated below, and it is specifically contemplated hereby that the flavor compositions of the present application can be used to modify or enhance the salty taste, umami taste, bitter taste, astringent mouthfeel and/or savory flavor of the following list edible compositions, either singly or in all reasonable combinations or mixtures thereof.

In certain embodiments, the food products to which the flavor compositions of the present application are admixed with comprise, by way of example, the wet soup category, the dehydrated and culinary food category, the beverage category, the frozen food category, the snack food category, and seasonings or seasoning blends, described herein.

In other embodiments, the flavor compositions of the present application are admixed with one or more confectioneries, chocolate confectionery, tablets, countlines, bagged selfmies/softlines, boxed assortments, standard boxed assortments, twist wrapped miniatures, seasonal chocolate, chocolate with toys, allsorts, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarised gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other rte cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, uht soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and Seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads.

7.1 Sweet Goods 7.1.1 Chewing Gum

The flavor systems can be used in sugarless gum formulations and can also be used in a sugar chewing gum. The flavor systems can be used in either regular chewing gum or bubble gum. Various specifics of chewing gum compositions are disclosed in U.S. Pat. No. 6,899,911, the disclosure of which is incorporated herein by reference in its entirety.

The chewing gum composition of the presently disclosed subject matter follows the general pattern outlined below. In general, a chewing gum composition typically contain a chewable gum base portion which is essentially free of water and is water-insoluble, a water-soluble bulk portion and flavors which are typically water insoluble. The water-soluble portion dissipates with a portion of the flavor over a period of time during chewing. The gum base portion is retained in the mouth throughout the chew.

The insoluble gum base generally comprises elastomers, elastomer solvents, plasticizers, waxes, emulsifiers and inorganic fillers. Plastic polymers, such as polyvinyl acetate, which behave somewhat as plasticizers, are also often included. Other plastic polymers that can be used include polyvinyl laureate, polyvinyl alcohol and polyvinyl pyrrolidone.

Elastomers can include polyisobutylene, butyl rubber, (isobutylene-isoprene copolymer) and styrene butadiene rubber, as well as natural latexes such as chicle. Elastomer solvents are often resins such as terpene resins. Plasticizers, sometimes called softeners, are typically fats and oils, including tallow, hydrogenated and partially hydrogenated vegetable oils, and cocoa butter. Commonly employed waxes include paraffin, microcrystalline and natural waxes such as beeswax and carnauba. Microcrystalline waxes, especially those with a high degree of crystallinity, can be considered bodying agents or textural modifiers.

According to the preferred embodiment of the presently disclosed subject matter, the insoluble gum base constitutes between about 5% to about 95% by weight of the gum. More preferably the insoluble gum base comprises between 10% and 50% by weight of the gum and most preferably about 20% to 35% by weight of the gum.

The gum base typically also includes a filler component. The filler component can be calcium carbonate, magnesium carbonate, talc, dicalcium phosphate or the like. The filler can constitute between about 5% and about 60% by weight of the gum base. Preferably the filler comprises about 5% to 50% by weight of the gum base.

Gum bases typically also contain softeners including glycerol monostearate and glycerol triacetate. Gum bases can also contain optional ingredients such as antioxidants, colors, and emulsifiers. The presently disclosed subject matter contemplates employing any commercially acceptable gum base.

The water-soluble portion of the chewing gum can further comprise softeners, sweeteners, flavors, physiological cooling agents and combinations thereof. The sweeteners often fulfill the role of bulking agents in the gum. The bulking agents typically comprise about 5% to about 95% of the gum composition.

Softeners are added to the chewing gum in order to optimize the chewability and mouth feel of the gum. Softeners, also known in the art as plasticizers or plasticizing agents, generally constitute between about 0.5% to about 15% of the chewing gum. Softeners contemplated by the presently disclosed subject matter include glycerin, lecithin and combinations thereof. Further, aqueous sweetener solutions such as those containing sorbitol, hydrogenated starch hydrolysate, corn syrup and combinations thereof can be used as softeners and binding agents in gum.

As mentioned above, the flavor systems of the presently disclosed subject matter can be used in sugarless gum formulations. However, formulations containing sugar are also within the scope of the invention. Sugar sweeteners generally include saccharide-containing components commonly known in the chewing gum art which comprise, but are not limited to, sucrose, dextrose, maltose, dextrin, dried invert sugar, fructose, galactose, corn syrup solids and the like, alone or in any combination.

The flavor systems of the presently disclosed subject matter can also be used in combination with sugarless sweeteners. Generally sugarless sweeteners include components with sweetening characteristics but which are devoid of the commonly known sugars and comprise, but are not limited to, sugar alcohols such as sorbitol, hydrogenated isomaltulose, mannitol, xylitol, lactitol, erythritol, hydrogenated starch hydrolysate, maltitol and the like alone or in any combination.

Depending on the particular sweetness release profile and shelf-stability needed, coated or uncoated high-intensity sweeteners can be used in the chewing gum composition, or can be used in a coating applied to centers made from those gum compositions. High-intensity sweeteners, preferably aspartame, can be used at levels from about 0.01% to about 3.0%. Encapsulated aspartame is a high intensity sweetener with improved stability and release characteristics, as compared to free aspartame. Free aspartame can also be added, and a combination of some free and encapsulated aspartame is preferred when aspartame is used. Other high intensity sweeteners that can be used in the gum center are: saccharin. Thaumatin, alitame, saccharin salts, sucralose, Stevia, and acesulfame K. Overall, the chewing gum composition will preferable comprise about 0.5% to about 90% sweetening agents. Most typically the sweetening agents will comprises at least one bulk sweetener and at least one high-intensity sweetener.

Optional ingredients such as colors, emulsifiers and pharmaceutical agents can also be added as separate components of the chewing gum composition, or added as part of the gum base.

Aqueous syrups, such as corn syrup and hydrogenated corn syrup can be used, particularly if their moisture content is reduced. This can preferably be done by coevaporating the aqueous syrup with a plasticizer, such as glycerin or propylene glycol, to a moisture content of less than 10%. Preferred compositions include hydrogenated starch hydrolysate solids and glycerin. Such syrups and their methods of preparation are discussed in detail in U.S. Pat. No. 4,671,967.

A preferred method of manufacturing chewing gum according to the presently disclosed subject matter is by sequentially adding the various chewing gum ingredients to any commercially available mixer known in the art. After the ingredients have been thoroughly mixed, the gum is discharged from the mixer and shaped into the desired form such as by rolling into sheets and cutting into sticks, extruding into chunks, or casting into pellets.

Generally, the ingredients are mixed by first melting the gum base and adding it to the running mixer. The base can also be melted in the mixer itself. Color or emulsifiers can also be added at this time, along with syrup and a portion of the bulking agent. Further portions of the bulking agent can then be added to the mixer. Flavor systems are typically added with the final portion of the bulking agent. If the flavor system is coated or otherwise modified as when incorporated into a delivery system to modify its release rate, it will preferably be added after the final portion of bulking agent has been added. The entire mixing procedure typically takes from five to twenty minutes, but longer mixing times can sometime be required. Those skilled in the art will recognize that many variations of the above described procedures can be followed.

If formed into pellets or balls, the chewing gum composition can be coated. The coating is initially present as a liquid syrup which contains from about 30% to about 80% or 85% sugars or sugar alcohols, and from about 15% or 20% to about 70% of a solvent such as water. In general, the coating process is carried out in conventional panning equipment. Gum center tablets to be coated are placed into the panning equipment to form a moving mass.

The material or syrup which will eventually form the coating is applied or distributed over the gum center tablets. The flavor systems of the presently disclosed subject matter can be added before, during and after applying the syrup to the gum centers. Once the coating has dried to form a hard surface, additional syrup additions can be made to produce a plurality of coatings or multiple layers of coating. The flavor systems can be added to any or none of the coatings and/or layers.

In the panning procedure, syrup is added to the gum center tablets at a temperature range of from about 100° F. to about 240° F. Preferably, the syrup temperature is from about 140° F. to about 200° F. Most preferably, the syrup temperature should be kept constant throughout the process in order to prevent the polyol in the syrup from crystallizing. The syrup can be mixed with, sprayed upon, poured over, or added to the gum center tablets in any way known to those skilled in the art.

In another embodiment, a soft coating is formed by adding a powder coating after a liquid coating. The powder coating can include natural carbohydrate gum hydrolysates, maltodextrin, gelatin, cellulose derivatives, starches, modified starches, sugars, sugar alcohols, natural carbohydrate gums and fillers like talc and calcium carbonate.

Each component of the coating on the gum center can be applied in a single layer or in a plurality of layers. In general, a plurality of layers is obtained by applying single coats, allowing the layers to dry, and then repeating the process. The amount of solids added by each coating step depends chiefly on the concentration of the coating syrup. Any number of coats can be applied to the gum center tablet. Preferably, no more than about 75 coats are applied to the gum center. More preferably, less than about 60 coats are applied and most preferably, about 30 to about 60 coats are applied. In any event, the presently disclosed subject matter contemplates applying an amount of syrup sufficient to yield a coated chewing gum product containing about 10% to about 65% coating. Preferably, the final product will contain from about 20% to about 50% coating.

Those skilled in the art will recognize that in order to obtain a plurality of coated layers, a plurality of premeasured aliquots of coating syrup can be applied to the gum center. It is contemplated, however, that the volume of aliquots of syrup applied to the gum center can vary throughout the coating procedure.

Once a coating of syrup is applied to the gum center, the syrup is dried in an inert medium. A preferred drying medium comprises air. Preferably, forced drying air contacts the wet syrup coating in a temperature range of from about 70° F. to about 110° F. More preferably, the drying air is in the temperature range of from about 80° F. to about 100° F. The invention also contemplates that the drying air possesses a relative humidity of less than about 15%. Preferably, the relative humidity of the drying air is less than about 8%.

The drying air can be passed over and admixed with the syrup coated gum centers in any way commonly known in the art. Preferably, the drying air is blown over and around the syrup coated gum center at a flow rate, for large scale operations, of about 2800 cubic feet per minute. If lower quantities of material are being processed, or if smaller equipment is used, lower flow rates would be used. If a flavor is applied after a syrup coating has been dried, the presently disclosed subject matter contemplates drying the flavor with or without the use of a drying medium.

The amount of flavoring agent employed herein is normally a matter of preference subject to such factors as the type of final chewing gum composition, the individual flavor, the gum base employed, and the strength of flavor desired. Thus, the amount of flavoring can be varied in order to obtain the result desired in the final product and such variations are within the capabilities of those skilled in the art without the need for undue experimentation. In gum compositions, the flavoring agent is generally present in amounts from about 0.02% to about 5%, and preferably from about 0.1% to about 2%, and more preferably, from about 0.8% to about 1.8%, by weight of the chewing gum composition.

7.1.2 Sugar Confectionary

Another important aspect of the presently disclosed subject matter includes a confectionery composition incorporating the inventive flavoring agent and a method for preparing the confectionery compositions. The preparation of confectionery formulations is well-known in the art. Confectionery items have been classified as either "hard" confectionery or "soft" confectionery. The flavoring agents of the presently disclosed subject matter can be incorporated into the confections by admixing the compositions of the presently disclosed subject matter into the conventional hard and soft confections.

Hard confectionery can be processed and formulated by conventional means. In general, a hard confectionery has a base composed of a mixture of sugar and other carbohydrate bulking agents kept in an amorphous or glassy condition. The hard confectionery can also be sugarless. This form is considered a solid syrup of sugars generally having from about 0.5% to about 1.5% moisture. Such materials normally contain up to about 92% sugar, up to about 55% corn syrup and from about 0.1% to about 5% water, by weight of the final composition. The syrup component is generally prepared from sucrose and corn syrups, but can include other materials. Further ingredients such as flavorings, sweetening agents, acidulants, colorants and so forth can also be added.

Such confectionery can be routinely prepared by conventional methods, including but not limited to methods involving fire cookers, vacuum cookers, and scraped-surface cookers also referred to as high speed atmospheric cookers. The apparatus useful in accordance with the presently disclosed subject matter comprises cooking and mixing apparatus well known in the confectionery manufacturing arts, and therefore the selection of the specific apparatus will be apparent to the artisan.

Fire cookers involve the traditional method of making a candy base. In this method, the desired quantity of carbohydrate bulking agent is dissolved in water by heating the agent in a kettle until the bulking agent dissolves. Additional bulking agent can then be added and cooked until a final temperature of 145° C. to 156° C. is achieved. The batch is then cooled and worked as a plastic-like mass to incorporate additives such as flavoring agent, colorants and the like.

A high-speed atmospheric cooker uses a heat-exchanger surface, which involves spreading a film of candy on a heat exchange surface, the candy is heated to 165° C. to 170° C. within a few seconds. The candy is then rapidly cooled to 100° C. to 120° C. and worked as a plastic-like mass enabling incorporation of the additives, such as flavoring agent, colorants and the like. In vacuum cookers, the carbohydrate bulking agent is boiled to 125° C. to 132° C., vacuum is applied and additional water is boiled off without extra heating. When cooking is complete, the mass is a semi-solid and has a plastic-like consistency. At this point, flavoring agent, colorants, and other additives are admixed in the mass by routine mechanical mixing operations.

The optimum mixing required to uniformly mix the flavoring agent, colorants and other additives during conventional manufacturing of hard confectionery is determined by the time needed to obtain a uniform distribution of the materials. Generally, mixing times of from 2 to 10 minutes have been found to be acceptable.

Once the candy mass has been properly tempered, it can be cut into workable portions or formed into desired shapes. A variety of forming techniques can be utilized depending upon the shape and size of the final product desired. A general discussion of the composition and preparation of hard confections can be found in H. A. Lieberman, Pharmaceutical Dosage Forms: Tablets, Volume 1 (1989), Marcel Dekker, Inc., New York, N.Y. at pages 419 to 582, which disclosure is incorporated herein by reference.

Compressed tablet confections contain particular materials and are formed into structures under pressure. These confections generally contain sugars in amounts up to about 95%, by weight of the composition, and typical tablet excipients such as binders and lubricants as well as flavoring agent, colorants and so forth. These confections can also be sugarless.

Similar to hard confectionery, soft confectionery can be utilized in the embodiments of the disclosed subject matter. The preparation of soft confections, such as nougat, involves conventional methods, such as the combination of two primary components, namely (1) a high boiling syrup such as a corn syrup, or the like, and (2) a relatively light textured frappe, generally prepared from egg albumin, gum arabic, gelatin, vegetable proteins, such as soy derived compounds, sugarless milk derived compounds such as milk proteins, and mixtures thereof. The frappe is generally relatively light, and can, for example, range in density from about 0.5 to about 0.7 grams/cc.

The high boiling syrup, or "bob syrup" of the soft confectionery is relatively viscous and has a higher density than the frappe component, and frequently contains a substantial amount of carbohydrate bulking agent. Conventionally, the final nougat composition is prepared by the addition of the "bob syrup" to the frappe under agitation, to form the basic nougat mixture. Further ingredients such as flavoring, additional carbohydrate bulking agent, colorants, preservatives, medicaments, mixtures thereof and the like can be added thereafter also under agitation. Soft confectioneries can also be prepared sugarless. A general discussion of the composition and preparation of nougat confections can be found in B. W. Minifie, Chocolate, Cocoa and Confectionery: Science and Technology, 2nd edition, AVI Publishing Co., Inc., Westport, Conn. (1983), at pages 576-580, which disclosure is incorporated herein by reference.

In general, the frappe component is prepared first and thereafter the syrup component is slowly added under agitation at a temperature of at least about 65° C., and preferably at least about 100° C. The mixture of components is continued to be mixed to form a uniform mixture, after which the mixture is cooled to a temperature below 80° C., at which point, the flavor can be added. The mixture is further mixed for an additional period until it is ready to be removed and formed into suitable confectionery shapes.

In accordance with this invention, effective amounts of the flavoring agents of the presently disclosed subject matter can be admixed into the hard and soft confections. The exact amount of flavoring agent employed is normally a matter of preference subject to such factors as the particular type of confection being prepared, the type of bulking agent or carrier employed, the type of flavor employed and the intensity of breath freshening perception desired. Thus, the amount of flavoring agent can be varied in order to obtain the result desired in the final product and such variations are within the capabilities of those skilled in the art without the need for undue experimentation. In general, the amount of flavoring agent normally present in a hard or soft confection will be from about 0.001% to about 20%, preferably from about 0.01% to about 15%, more preferably from about 0.01% to about 10%, and more preferably from about 0.01% to about 5%, and more preferably 0.01% to about 0.5% by weight of the confection.

The presently disclosed subject matter extends to methods for making the improved confections. The flavoring agents can be incorporated into an otherwise conventional hard or soft confection composition using standard techniques and equipment known to those skilled in the art. The apparatus useful in accordance with the presently disclosed subject matter comprises mixing and heating apparatus well known in the confectionery manufacturing arts, and therefore the selection of the specific apparatus will be apparent to the artisan.

In such a method, a composition is made by admixing the inventive flavoring agent into the confectionery composition along with the other ingredients of the final desired composition. Other ingredients will usually be incorporated into the composition as dictated by the nature of the desired composition as well known by those having ordinary skill in the art. The ultimate confectionery compositions are readily prepared using methods generally known in the food technology and pharmaceutical arts. Thereafter the confectionery mixture can be formed into desirable confectionery shapes.

The flavoring agents can be formulated with conventional ingredients which offer a variety of textures to suit particular applications. Such ingredients can be in the form of hard and soft confections, tablets, toffee, nougat, chewy candy, chewing gum and so forth, center filled candies, both sugar and sugarless. The acceptable ingredients can be selected from a wide range of materials. Without being limited thereto, such materials include diluents, binders and adhesives, lubricants, disintegrants, bulking agents, humectants and buffers and adsorbents. The preparation of such confections and chewing gum products is well known.

7.1.3 Chocolates and Fillings

The presently disclosed subject matter is also used with and/or in chocolate products, chocolate-flavored confections, and chocolate flavored compositions. Chocolates also include those containing crumb solids or solids fully or partially made by a crumb process. Various chocolates are disclosed, for example, in U.S. Pat. Nos. 7,968,140 and 8,263,168, the disclosures of which are incorporated herein by reference in their entireties. A general discussion of the composition and preparation of chocolate confections can be found in B. W. Minifie, Chocolate, Cocoa and Confectionery: Science and Technology, 2nd edition, AVI Publishing Co., Inc., Westport, Conn. (1982), which disclosure is incorporated herein by reference.

The term "chocolate" as used herein refers to a solid or semi-plastic food and is intended to refer to all chocolate or chocolate-like compositions containing a fat-based component phase or fat-like composition. The term is intended to include standardized or nonstandardized compositions conforming to the U.S. Standards Of Identity (SOI), CODEX Alimentarius and/or other international standards and compositions not conforming to the U.S. Standards Of Identity or other international standards. The term includes dark chocolate, baking chocolate, sweet chocolate, bittersweet or semisweet chocolate, milk chocolate, buttermilk chocolate, skim milk chocolate, mixed dairy product chocolate, white chocolate, sweet cocoa and vegetable fat coating, sweet chocolate and vegetable fat coating, milk chocolate and vegetable fat coating, vegetable fat based coating, pastels including white chocolate or coating made with cocoa butter or vegetable fat or a combination of these, nutritionally modified chocolate-like compositions (chocolates or coatings made with reduced calorie ingredients) and low fat chocolates, aerated chocolates, compound coatings, non-standardized chocolates and chocolate-like compositions, unless specifically identified otherwise.

Nonstandardized chocolates result when, for example, the nutritive carbohydrate sweetener is replaced partially or completely; or when the cocoa butter, cocoa butter alternative, cocoa butter equivalent, cocoa butter extender, cocoa butter replacer, cocoa butter substitute or milkfat are replaced partially or completely; or when components that have flavors that imitate milk, butter or chocolate are added or other additions or deletions in formula are made outside the FDA standards of identify of chocolate or combinations thereof. Chocolate-like compositions are those fat-based compositions that can be used as substitutes for chocolate in applications such as panning, molding, or enrobing; for example, carob.

In the United States, chocolate is subject to a standard of identity established by the U.S. Food and Drug Administration (FDA) under the Federal Food, Drug and Cosmetic Act. Definitions and standards for the various types of chocolate are well established in the U.S. Nonstandardized chocolates are those chocolates which have compositions that fall outside the specified ranges of the standardized chocolates.

The chocolate can contain a sugar syrup/solids, invert sugar, hydrolyzed lactose, maple sugar, brown sugar, molasses, honey, sugar substitute and the like. The term "sugar substitute" includes bulking agents, sugar alcohols (polyols such as glycerol), or high potency sweeteners or combinations thereof. Nutritive carbohydrate sweeteners with varying degrees of sweetness intensity can be any of those typically used in the art and include, but are not limited to, sucrose, e.g., from cane or beet, dextrose, fructose, lactose, maltose, glucose syrup solids, corn syrup solids, invert sugar, hydrolyzed lactose, honey, maple sugar, brown sugar, molasses and the like. Sugar substitutes can partially replace the nutritive carbohydrate sweetener. High potency sweeteners include aspartame, cyclamates, saccharin, acesulfame-K, neohesperidin dihydrochalcone, sucralose, alitame, stevia sweeteners, glycyrrhizin, thaumatin and the like and mixtures thereof. The preferred high potency sweeteners are aspartame, cyclamates, saccharin, and acesulfame-K. Examples of sugar alcohols can be any of those typically used in the art and include sorbitol, mannitol, xylitol, maltitol, isomalt, lactitol and the like.

The chocolates can also contain bulking agents. The term "bulking agents" as defined herein can be any of those typically used in the art and include polydextrose, cellulose and its derivatives, maltodextrin, gum arabic, and the like.

The chocolate products can contain emulsifiers. Examples of safe and suitable emulsifiers can be any of those typically used in the art and include lecithin derived from vegetable sources such as soybean, safflower, corn, etc., fractionated lecithins enriched in either phosphatidyl choline or phosphatidyl ethanolamine, or both, mono- and diglycerides, diacetyl tartaric acid esters of mono- and diglycerides (also referred to as DATEM), monosodium phosphate derivatives of mono- and diglycerides of edible fats or oils, sorbitan monostearate, hydroxylated lecithin, lactylated fatty acid esters of glycerol and propylene glycol, polyglycerol esters of fatty acids, propylene glycol mono- and di-esters of fats and fatty acids, or emulsifiers that can become approved for the US FDA-defined soft candy category. In addition, other emulsifiers that can be used include polyglycerol polyricinoleate (PGPR), ammonium salts of phosphatidic acid, (e.g., YN) sucrose esters, oat extract, etc., any emulsifier found to be suitable in chocolate or similar fat/solid system or any blend.

The term "chocolate-flavored confection" refers to food products, excluding "chocolate", having a chocolate flavor/aroma and comprising a cocoa fraction. These products are stable at ambient temperatures for extended periods of time (e.g., greater than 1 week) and are characterized as microbiologically shelf-stable at 18-30° C. under normal atmospheric conditions. Examples include chocolate-flavored hard candies, chewables, chewing gums, etc.

The term "chocolate-flavored compositions" refers to chocolate-flavored compositions, excluding "chocolate", containing a cocoa fraction and having a chocolate flavor/aroma. Examples include chocolate-flavored cake mixes, ice creams, syrups, baking goods, etc. The term includes chocolate-flavored compositions (e.g., cakes, nougats, puddings, etc.), as well as compositions not having a chocolate-flavor (e.g., caramels, etc.).

7.2 Savory Goods and Other Food Products

In certain embodiments, the flavor compositions of the present application are incorporated into savory goods to impart, enhance, or modify a salty taste, umami taste, bitter taste, astringent mouthfeel and/or savory taste. In certain embodiments, a savory good is a food product that has savory flavors including, for example, but not limited to, spicy flavor, pepper flavor, dairy flavor, vegetable flavor, tomato flavor, dill flavor, meat flavor, poultry flavor, chicken flavor and reaction flavors that are added or generated during heating of a food product.

In certain embodiments, the flavor compositions are incorporated into a wet soup category food product, which comprises wet/liquid soups regardless of concentration or container, including frozen soups. In certain embodiments, a soup food product means a food prepared from meat, poultry, fish, vegetables, grains, fruit and/or other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

In certain embodiments, the flavor compositions of the present application are incorporated into a dehydrated and culinary food category of food products, which comprises (i) cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

In certain embodiments, the flavor compositions of the present application are incorporated into a meat food product. In certain embodiments, meat food products include food product made by processing the edible remains of any dead animal, including birds, fish, crustaceans, shellfish and mammals. Meat food products include, without limitation, for example, prepared beef, lamb, pork, poultry or seafood products. Examples of such meat food products include, for example, bologna, frankfurters, sausage, luncheon, deli slices, loaves, bacon, meatballs, fish sticks, chicken fingers, and ground meats, e.g., meatloaf, meatballs and hamburgers. A meat food product may be combined with a simulated meat food product. Simulated meat food products include, without limitation, for example, a meat alternative, meat analog, soy burger, soy bologna, soy frankfurter, soy sausage, soy luncheon loaves, soy bacon and soy meatball. A simulated meat food product may be combined with a meat food product.

In certain embodiments, the flavor compositions of the present application are incorporated into a snack food category food product. In certain embodiments, snack food products include any food that can be a light informal meal including, but not limited to sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

In certain embodiments, the flavor compositions of the present application are incorporated into frozen of food products, which comprises chilled or frozen food products, for example, but not limited to, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, frozen ready meals, frozen pizza, chilled pizza, frozen soup, frozen pasta, frozen processed red meat, frozen processed poultry, frozen processed fish/seafood, frozen processed vegetables, frozen meat substitutes, frozen potatoes, frozen bakery products and frozen desserts.

In certain embodiments, the flavor compositions of the present application are incorporated into food products for animal consumption. This includes food or drinks (liquids) for consumption by agricultural animals, pets and zoo animals.

The presently disclosed subject matter can be used in a variety of food products. The term "food product" includes any food product, for example, those set forth in 21 CFR 101.12. Nonlimiting examples of such food products include frozen desserts, baked goods, fillings, nutritional drinks, beverages, salad dressing or similar dressing, sauces, icings, puddings and custards, batters, and the like. Various baked goods are disclosed in U.S. Pat. No. 6,536,599, the disclosure of which is herein incorporated by reference in its entirety. Non-limiting examples of bakery goods includes cookies, cakes, rolls, pastries, pie dough, brownies, breads, bagels and the like. The flavor compositions are also suitable as a component in frozen foods.

7.3 Pharmaceuticals

The flavoring compositions can also be in the form of a pharmaceutical. One non-limiting example of a pharmaceutical form is a suspension. Pharmaceutical suspensions can be prepared by conventional compounding methods. Suspensions can contain adjunct materials employed in formulating the suspensions of the art. The suspensions of the presently disclosed subject matter can comprise preservatives, buffers, suspending agents, antifoaming agents, sweetening agents, flavoring agents, coloring or decoloring agents, solubilizers, and combinations thereof.

Flavoring agents such as those flavors well known to the skilled artisan, such as natural and artificial flavors and mints, such as peppermint, menthol, citrus flavors such as orange and lemon, artificial vanilla, cinnamon, various fruit flavors, both individual and mixed and the like can be utilized in amounts from about 0.01% to about 5%, and more preferably 0.01% to about 0.5% by weight of the suspension.

The pharmaceutical suspensions of the presently disclosed subject matter can be prepared as follows: (A) admix the thickener with water heated from about 40° C. to about 95° C., preferably from about 40° C. to about 70° C., to form a dispersion if the thickener is not water soluble or a solution if the thickener is water soluble; (B) admix the sweetening agent with water to form a solution; (C) admix the flavoring agent with the thickener-water admixture to form a uniform thickener-flavoring agent; (D) combine the sweetener solution with the thickener-flavoring agent and mix until uniform; and (E) admix the optional adjunct materials such as coloring agents, flavoring agents, decolorants, solubilizers, antifoaming agents, buffers and additional water with the mixture of step (D) to form the suspension.

The flavoring compositions can also be in chewable form. To achieve acceptable stability and quality as well as good taste and mouth feel in a chewable formulation several considerations are important. These considerations include the amount of active substance per tablet, the flavoring agent employed, the degree of compressibility of the tablet and additional properties of the composition.

Chewable pharmaceutical candy is prepared by procedures similar to those used to make soft confectionery. A general discussion of the lozenge and chewable tablet forms of confectionery can be found in H. A. Lieberman and L. Lachman, Pharmaceutical Dosage Forms: Tablets Volume 1, Marcel Dekker, Inc., New York, N.Y. (1989) at pages 367 to 418, which disclosure is incorporated herein by reference. In a typical procedure, a boiled sugar-corn syrup blend is formed to which is added a frappe mixture. The boiled sugar-corn syrup blend can be prepared from sugar and corn syrup blended in parts by weight ratio of about 90:10 to about 10:90. The sugar-corn syrup blend is heated to temperatures above about 120° C. to remove water and to form a molten mass. The frappe is generally prepared from gelatin, egg albumin, milk proteins such as casein, and vegetable proteins such as soy protein, and the like, which is added to a gelatin solution and rapidly mixed at ambient temperature to form an aerated sponge like mass. The frappe is then added to the molten candy mass and mixed until homogeneous at temperatures between about 65° C. and about 120° C. The flavor composition can then be added to the homogeneous mixture as the temperature is lowered to about 65° C.-95° C. whereupon additional ingredients can then be added such as flavoring agents and coloring agents. The formulation is further cooled and formed into pieces of desired dimensions.

In other pharmaceutical embodiments, the flavoring agent is incorporated into an ingestible topical vehicle which can be in the form of a mouthwash, rinse, ingestible spray, suspension, dental gel, and the like. Typical non-toxic ingestible vehicles known in the pharmaceutical arts can be used in the presently disclosed subject matter. The preferred ingestible vehicles are water, ethanol, and water-ethanol mixtures. The water-ethanol mixtures are generally employed in a weight ratio from about 1:1 to about 20:1, preferably from about 3:1 to about 20:1, and most preferably from about 3:1 to about 10:1, respectively. The pH value of the ingestible vehicle is generally from about 4 to about 7, and preferably from about 5 to about 6.5. An ingestible topical vehicle having a pH value below about 4 is generally irritating to the ingestible cavity and an ingestible vehicle having a pH value greater than about 7 generally results in an unpleasant mouth feel.

The ingestible topical flavoring agents can also contain conventional additives normally employed in those products. Conventional additives include a fluorine providing compound, a sweetening agent, a flavoring agent, a coloring agent, a humectant, a buffer, and an emulsifier, providing the additives do not interfere with the flavoring properties of the composition. The coloring agents and humectants, and the amounts of these additives to be employed, set out above, can be used in the ingestible topical composition.

The flavoring agents (flavors, flavorants) which can be used include those flavors known to the skilled artisan, such as natural and artificial flavors. Suitable flavoring agents include mints, such as peppermint, citrus flavors such as orange and lemon, artificial vanilla, cinnamon, various fruit flavors, both individual and mixed, and the like.

The amount of flavoring agent employed in the ingestible topical composition is normally a matter of preference subject to such factors as the type of final ingestible composition, the individual flavor employed, and the strength of flavor desired. Thus, the amount of flavoring can be varied in order to obtain the result desired in the final product and such variations are within the capabilities of those skilled in the art without the need for undue experimentation. The flavoring agents, when used, are generally utilized in amounts that can, for example, range in amounts from about 0.05% to about 6%, by weight of the ingestible topical composition.

In accordance with the presently disclosed subject matter, effective amounts of the flavoring agents of the presently disclosed subject matter can be admixed with an ingestible topical vehicle to form a topical composition. These amounts are readily determined by those skilled in the art without the need for undue experimentation. In a preferred embodiment, the ingestible topical flavoring agents will comprise the flavoring agent in an amount from about 0.025% to about 2% and an ingestible topical vehicle in a quantity sufficient to bring the total amount of composition to 100%, by weight of the ingestible topical composition. In a more preferred embodiment, the ingestible topical flavoring agents will comprise the flavoring agent in an amount from about 0.05% to about 1% and an ingestible topical vehicle in a quantity sufficient to bring the total amount of composition to 100%, by weight of the ingestible topical composition.

The presently disclosed subject matter extends to methods for preparing the ingestible topical flavoring agents. In such a method, the ingestible topical composition is prepared by admixing an effective amount of the flavoring agent of the presently disclosed subject matter and an ingestible topical vehicle. The final compositions are readily prepared using standard methods and apparatus generally known by those skilled in the pharmaceutical arts. The apparatus useful in accordance with the presently disclosed subject matter comprises mixing apparatus well known in the pharmaceutical arts, and therefore the selection of the specific apparatus will be apparent to the artisan.

8. Methods of Measuring Taste and Texture Attributes

In certain embodiments of the present application, the taste and texture attributes of a food product can be modified by admixing a flavor composition with the food product as described herein. In certain embodiments, the attribute(s) can be enhanced or reduced by increasing or decreasing the concentration of the flavor composition admixed with the food product. In certain embodiments, the taste or texture attributes of the modified food product can be evaluated as described herein, and the concentration of flavor composition admixed with the food product can be increased or decreased based on the results of the evaluation.

Taste and texture attributes can be reliably and reproducibly measured using sensory analysis methods known as descriptive analysis techniques. The Spectrum™ method of descriptive analysis is described in Morten Meilgaard, D. Sc. et al., Sensory Evaluation Techniques (3d ed. 1999). The Spectrum™ method is a custom design approach meaning that the highly trained panelists who generate the data also develop the terminology to measure the attributes of interest. Further, the method uses intensity scales created to capture the intensity differences being investigated. These intensity scales are anchored to a set of well-chosen references. Using these references helps make the data universally understandable and usable over time. This ability to reproduce the results at another time and with another panel makes the data potentially more valuable than analytical techniques which offer similar reproducibility but lack the ability to fully capture the integrated sensory experiences as perceived by humans.

When conducting quantitative descriptive analysis for compounds that modify other compounds, the testing methodology can be adapted to capture the change in character and intensity of the modified compound. For example, when testing for compounds that modify the saltiness of other compounds, the panelists may first taste a salt reference of agreed upon saltiness in order to establish a reference point for comparison. After tasting the reference, panelists may taste and score the test sample for saltiness as well as any other basic taste, chemical feeling factor, or aromatic notes. To quantify any increase in salt perception, the panelists may then re-taste the reference and again assign scores for saltiness as well as any other basic taste, chemical feeling factor, or aromatic notes. To quantify any lingering aftertaste, panelists may re-taste the salt reference at 1 minute intervals until their saltiness perception returns to the level of the reference. During the aftertaste evaluations, the panelists also note and score any other basic taste, chemical feeling factor, or aromatic notes.

9. Methods of Synthesis

In certain embodiments, the peptides of the present application can be synthesized using standard chemosynthesis processes. In certain embodiments, the chemosynthesis process provides a peptide having a purity of at least 99.999%, or at least 99%, or at least 95%, or at least 90%, or at least 85%, or at least 80%. In certain embodiments, the peptides can be prepared using standard hydrolysis processes such as those employing acids, enzymes, or a combination of acids and enzymes.

In certain embodiments, the chemosynthesis process comprises synthesizing the peptides of the present application through the use of amino acid resins and/or deprotecting and coupling reactions. In certain embodiments, the peptides are synthesized using and automated peptide synthesizer using techniques known to those skilled in the art.

In certain embodiments the peptides of the present application are prepared from a food product source that is fractionated and/or extracted to form an enriched peptide composition comprising the peptides. In certain embodiments, the enriched peptide composition comprises the flavor composition of the present application and is admixed with a food product according to the methods of the present application. In other embodiments, the enriched peptide composition is combined with other compositions to form the flavor composition of the present application, which is then admixed with the food product according to the methods of the present application.

In certain embodiments the peptides of the present application are prepared from a food product source that is hydrolyzed to form a hydrolysate comprising the peptides. In certain embodiments, the food product source is hydrolyzed for between about 0.5 and about 15 hours, or between about 2 and about 13 hours, or between about 4 and about 11 hours, or between about 6 and about 9 hours. In certain embodiments, the hydrolysate comprises the flavor composition of the present application and is admixed with a food product according to the methods of the present application. In other embodiments, the hydrolysate is combined with other compositions to form the flavor composition of the present application, which is then admixed with the food product according to the methods of the present application.

In certain embodiments the peptides of the present application are prepared from a food product source that has been subject to fermentation and/or germination.

In certain embodiments the peptides of the present application are prepared from a food product source that is hydrolyzed and fractionated and/or extracted to form an enriched peptide hydrolysate composition comprising the peptides. In certain embodiments, the enriched peptide hydrolysate composition comprises the flavor composition of the present application and is admixed with a food product according to the methods of the present application. In other embodiments, the enriched peptide hydrolysate composition is combined with other compositions to form the flavor composition of the present application, which is then admixed with the food product according to the methods of the present application.

EXAMPLES

The presently disclosed subject matter will be better understood by reference to the following Examples, which are provided as exemplary of the invention, and not by way of limitation.

Example 1—Overfermented Cocoa Beans—a Novel Source of Taste Modulators

Recently overfermented cocoa beans were found to be a rich source of previously unknown salt taste and umami enhancing substances. Generally, there is a need for natural compounds, which are able to maintain or even improve the taste and palatability of food products. Therefore, the so called SENSOMICS approach was applied on the identification of further taste modulators with focus on saltiness, umami and kokumi.

An activity-guided fractionation in combination with comparative taste dilution analysis (cTDA) of an aqueous extract of overfermented cocoa beans revealed the presence of a series of small peptides containing either proline or pyro-glutamic acid. Structure elucidation was performed by means of UPLC-TOF-ESI-MS$^e$ and LC-MS/MS. Sensory experiments showed either umami or salt enhancing properties of these peptides and taste threshold concentrations were determined to fully describe the taste modulating activity.

In order to identify and quantitate the whole series of proline or pyro-glutamic acid dipeptides an UPLC-ESI-MS/MS$_{MRM}$ method was developed, respectively. These methods were applied on various cocoa samples with different times of fermentation as well as on further natural samples like hydrolyzed vegetable proteins.

Example 2—Novel Taste Modulators Identified from Overfermented Cocoa Beans

Novel taste enhancing compounds were identified in over-fermented cocoa. Sensory studies were conducted to characterize their mechanisms of action. HTP mass spectrometric profiling and quantitation of taste enhancing molecules were performed in various sources. Exploration of the chemistry and psychophysical properties of taste enhancing molecules were focused on umami, kokumi and salt modulation.

Raw materials used in this example included overfermented cocoa beans—14 day beans (fermented for 14 days and unroasted), chocolate liquor—liquor B (overfermented, roasted, steam-treatment and dried) and hydrolyzed cocoa powder—HCP (fermented, roasted, dried, defatted and treated with acid hydrolysis).

The raw materials were finely grounded and defatted with n-pentane. The components of the insoluble residue was extracted with acetone/water. The components of the aqueous solution was extracted with DCM and EtOAc and lyophilized.

Figure 2:
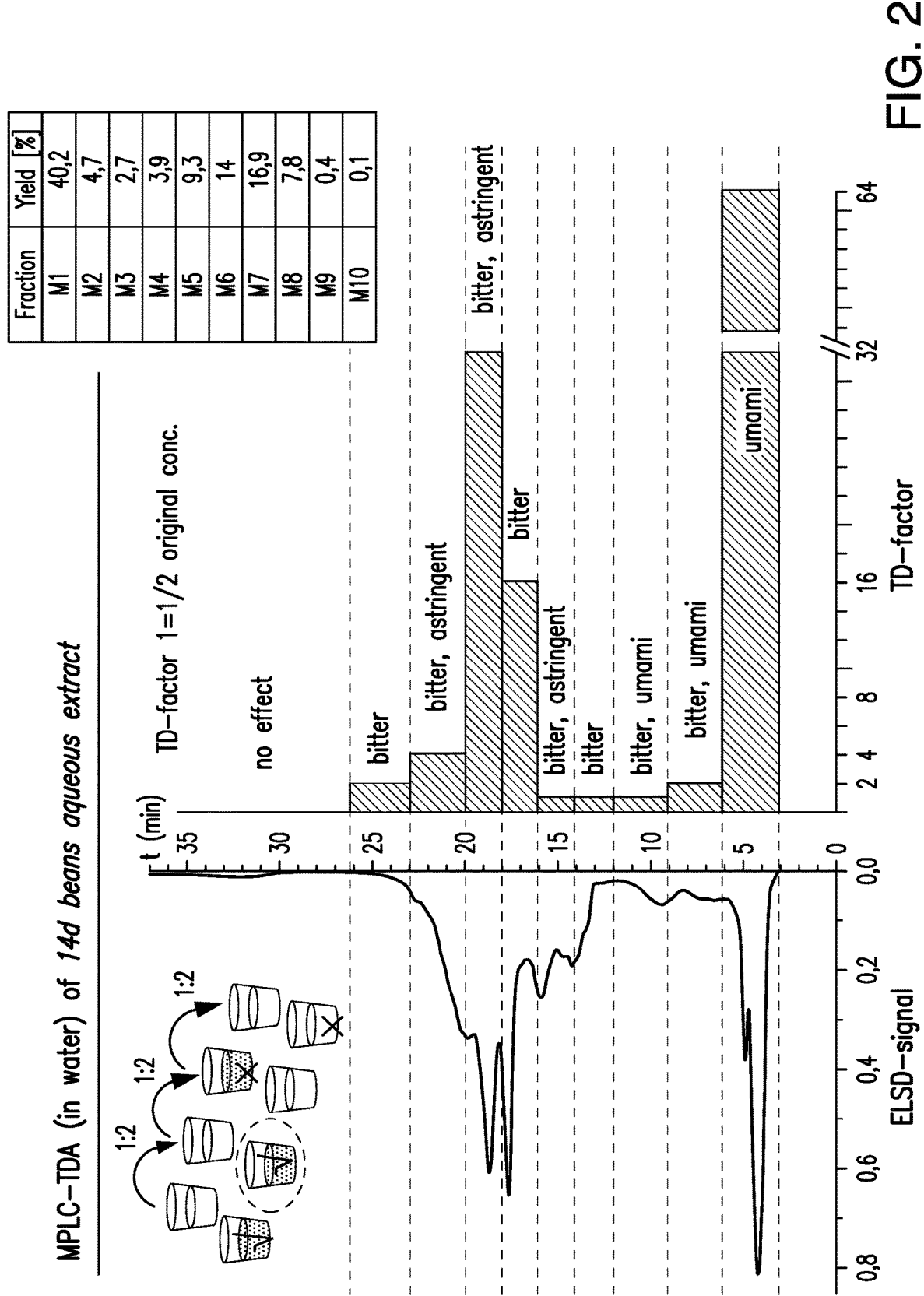
FIG. 2 depicts results of taste dilution analyses of various fractions of the aqueous extract of 14 day beans in water solution.
Figure 3:
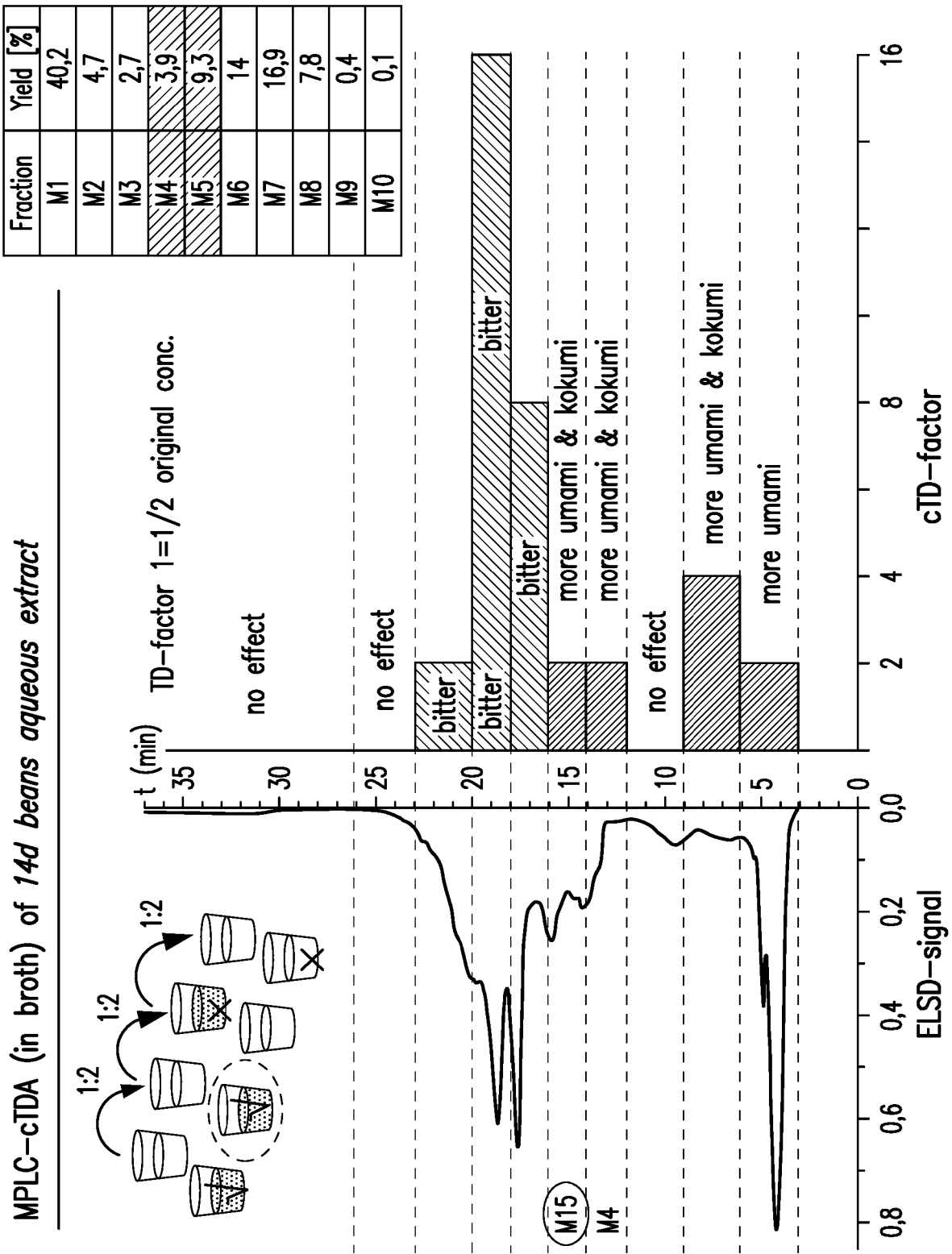
FIG. 3 depicts results of taste dilution analyses of various fractions of the aqueous extract of 14 day beans in model broth.

Medium pressure liquid chromatography (MPLC) were used to separate the components of the aqueous extract of 14 d beans. Various fractions are shown in FIG. 1. Taste dilution analysis (TDA) of each fraction was conducted in both water solution and in model broth (10 mM MSG and 50 mM NaCl). Different concentrations of samples were presented to 8-10 panelists wearing nose clip in dilution series (duo or trio tests with fixed reference). FIGS. 2 and 3 show that fractions M4 and M5 were able to enhance an umami taste and a kokumi taste in model broth, but not in water.

Figure 4:
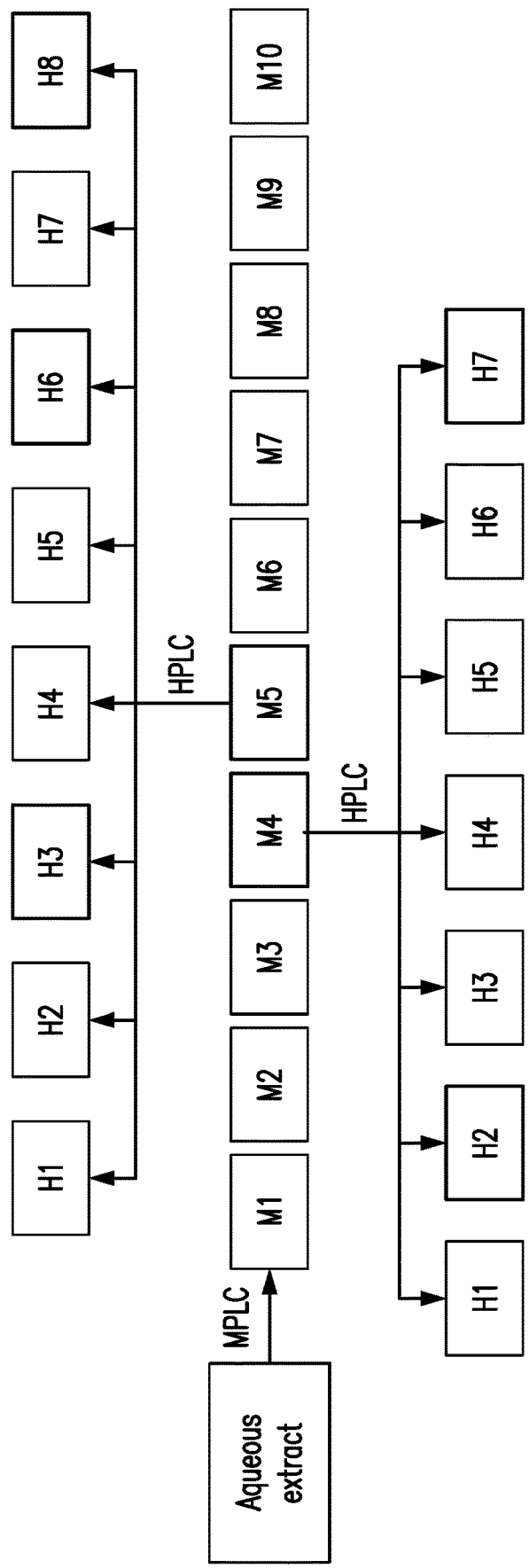
FIG. 4 depicts various fractions and subfractions of the aqueous extract of 14 day beans that exhibit taste modulating effects.

The components of M4 and M5 were further separated using high-performance liquid chromatography (HPLC), whereby various subfractions were obtained as shown in FIG. 4. TDA of each subfraction was conducted as described above, wherein subfractions H2 and H7 of M4 and subfractions H3, H6 and H8 of M5 showed taste enhancing/modulating effects.

LC-MS-TOF and MS/MS analyses were conducted to each subfraction to identify possible taste modulating substances in subfractions of M4 and M5. Table 1 shows the taste modulating peptides identified therefrom.

TABLE 1

| Fraction | Peptide |
| --- | --- |
| 14dM4H2 | pEEE |
|  | pEQAT |

TABLE 1-continued

| Fraction | Peptide |
| --- | --- |
| 14dM4H7 | VPA |
|  | RMP |
|  | DYR |
| 14dM5H3 | YGDG |
| 14dM5H6 | SPV |
|  | KDQP |
| 14dM5H8 | FE |
|  | NNAL |
|  | YV |
|  | NGGLQ |

Sensory analyses of certain identified peptides were conducted and results were shown in Table 2.

TABLE 2

| Peptide | Threshold Concentration in Model Broth (µM) | Taste Effect |
| --- | --- | --- |
| pEEE (pGlu-Glu-Glu) | 55 | Salt enhancing |
| pEQAT (pGlu-Gln-Ala-Thr) | 159 | Salt enhancing |
| VPA (Val-Pro-Ala) | 90 | Kokumi |
| RMP (Arg-Met-Pro) | 190 | Salt enhancing |
| NGGLQ (Asn-Gly-Gly-Leu-Gln) | 160 | Kokumi |
| NNAL (Asn-Asn-Ala-Leu) | 270 | Salt enhancing |
| FE (Phe-Glu) | 1050 | Sour |

Example 3—Identification of Prolyl Dipeptides as Taste Modulators

In addition to the various peptides disclosed in Example 2, dipeptide Val-Pro was identified from overfermented cocoa beans (subfraction M4H7) using separation and analytical methods described above. TDA analyses was subsequently conducted, where Val-Pro showed no taste activity in water below concentrations of 5.0 mM, but a salt enhancing taste effect in model broth with a threshold concentration of 0.8 mM.

Figure 5A:
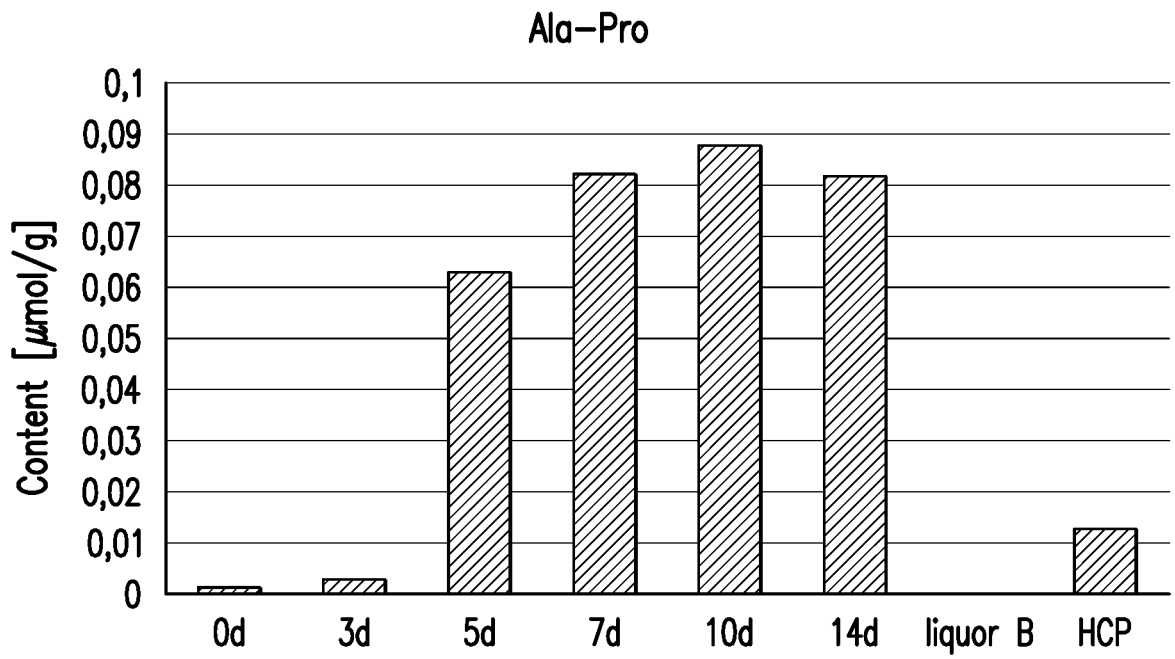
FIGS. 5A and 5B depict that Ala-Pro and Pro-Ala peptides were present at a similar concentration in different fermentation samples of cocoa beans.
Figure 5B:
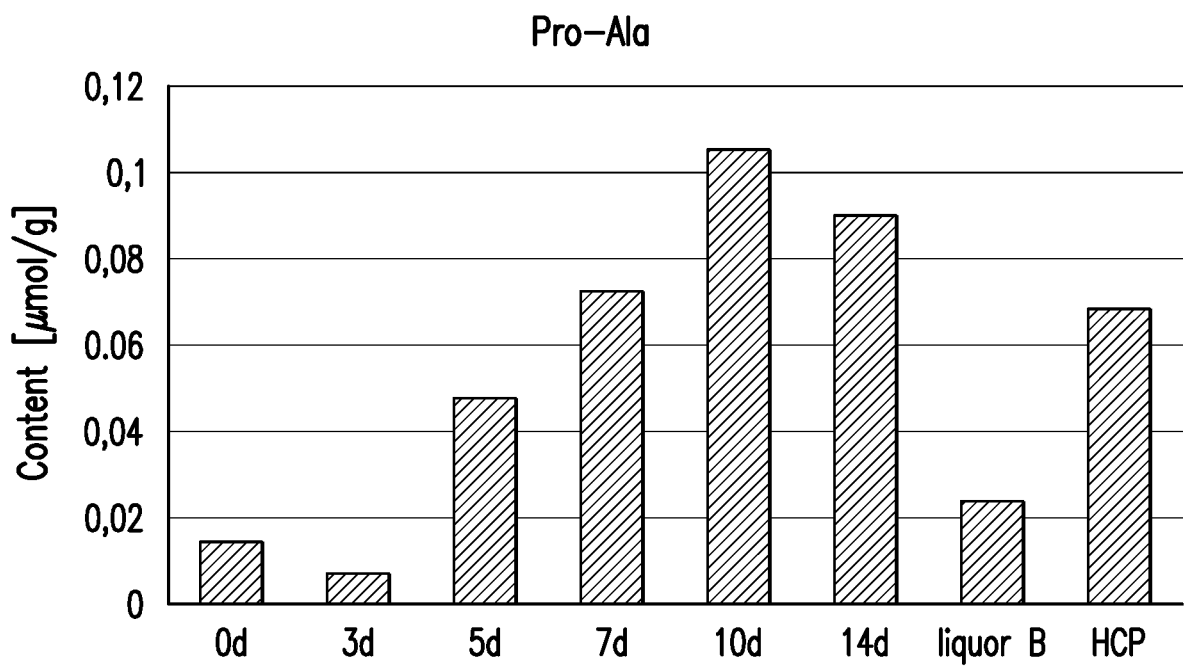
Figure 5C:
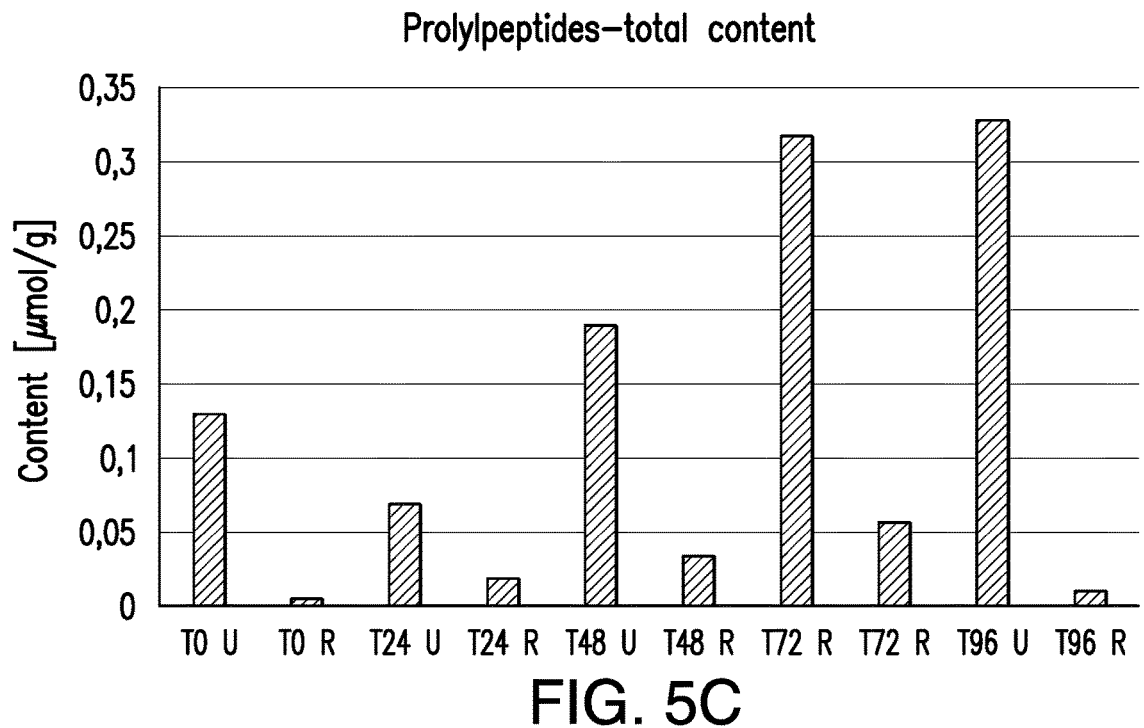
FIG. 5C depicts that total content of prolyl peptides in cocoa samples increased with time of germination, whereas roasting process decreased the content of prolyl peptides. The numbers at the x-axis indicate hours of germination process. R: roasted; U: unroasted.
Figure 5D:
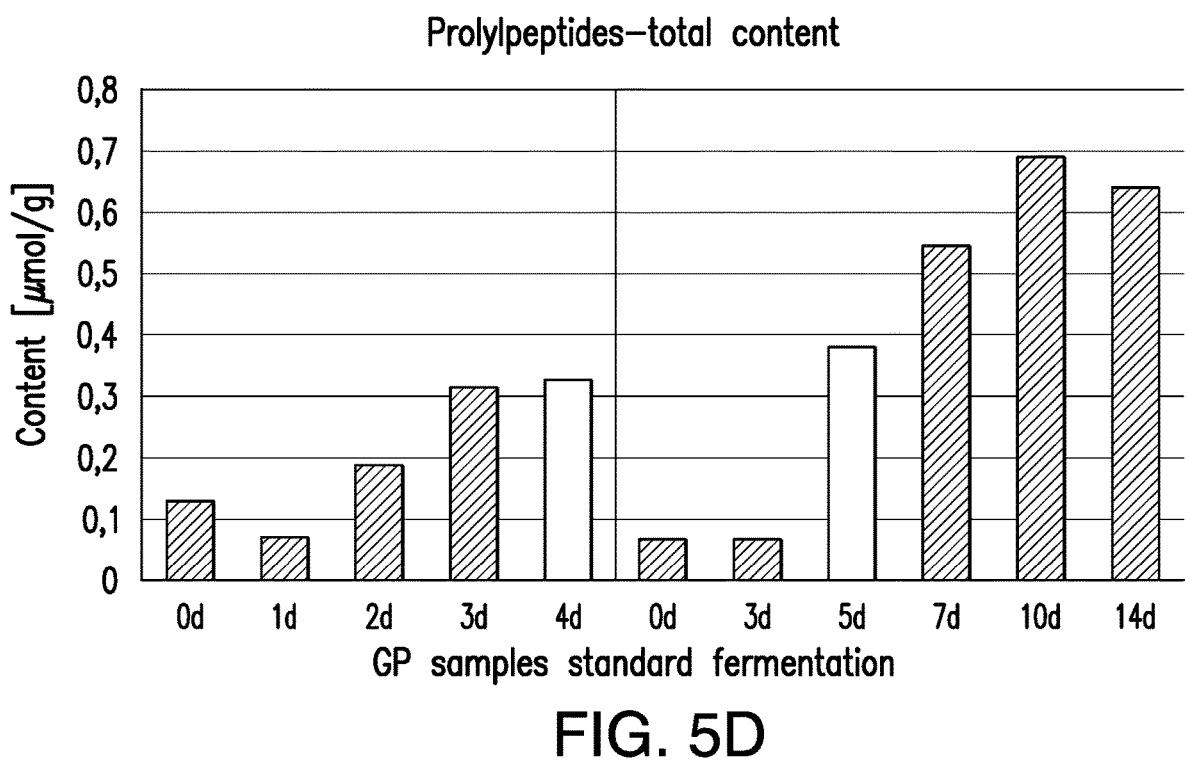
FIG. 5D shows that prolyl peptides were more rapidly generated by germination compared to fermentation.

Moreover, Ala-Pro and Pro-Ala were identified in different fermentation samples of cocoa beans described above. FIGS. 5A and 5B show these peptides were present at a similar concentration in different fermentation samples. The concentrations in fermented cocoa beans increases with time of fermentation and reaches a maximum at 10 days, and the concentrations in HCP and chocolate liquor strongly differ. Furthermore, FIG. 5C shows that cocoa samples that were subjected to germination process contained prolyl dipeptides, and total content of prolyl-peptides increased with time of germination, whereas prolyl-dipeptides were degraded by roasting process. FIG. 5D shows that prolyl peptides were more rapidly generated by germination compared to fermentation.

Figure 6:
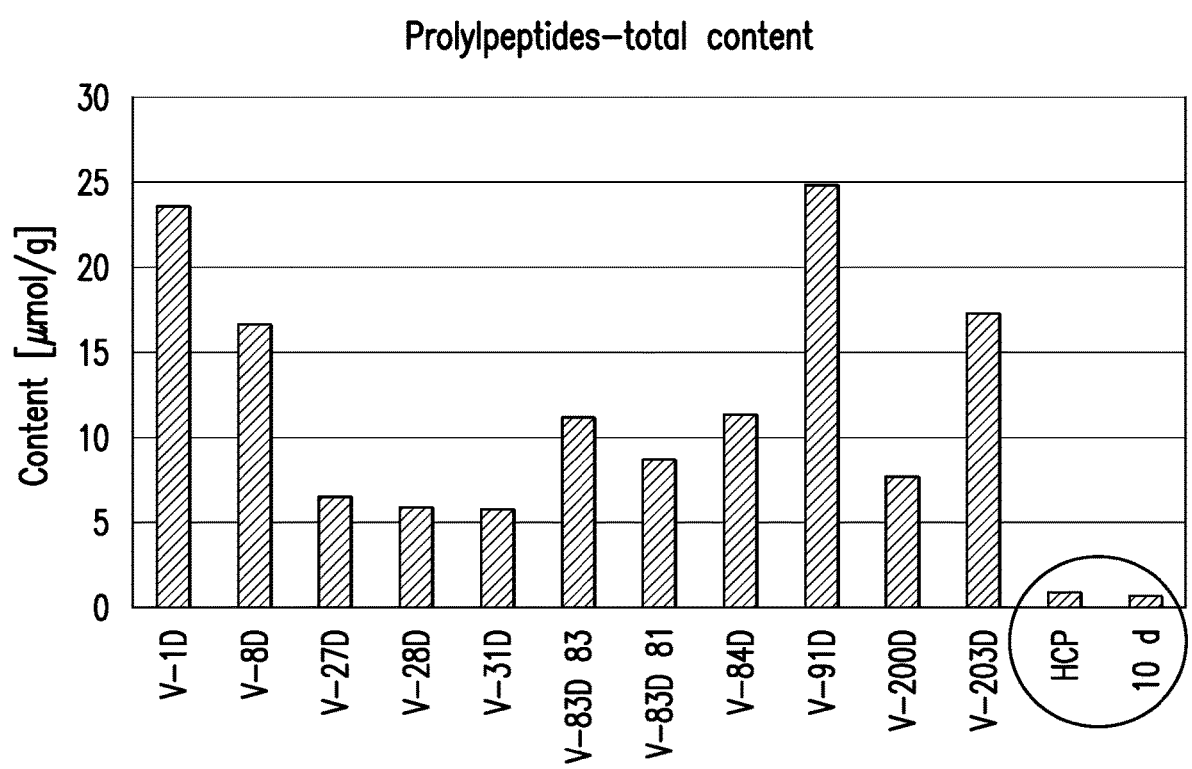
FIG. 6 depicts the concentrations of prolyl peptides in hydrolyzed vegetable proteins (HVP) samples compared to cocoa samples.
Figure 7A:
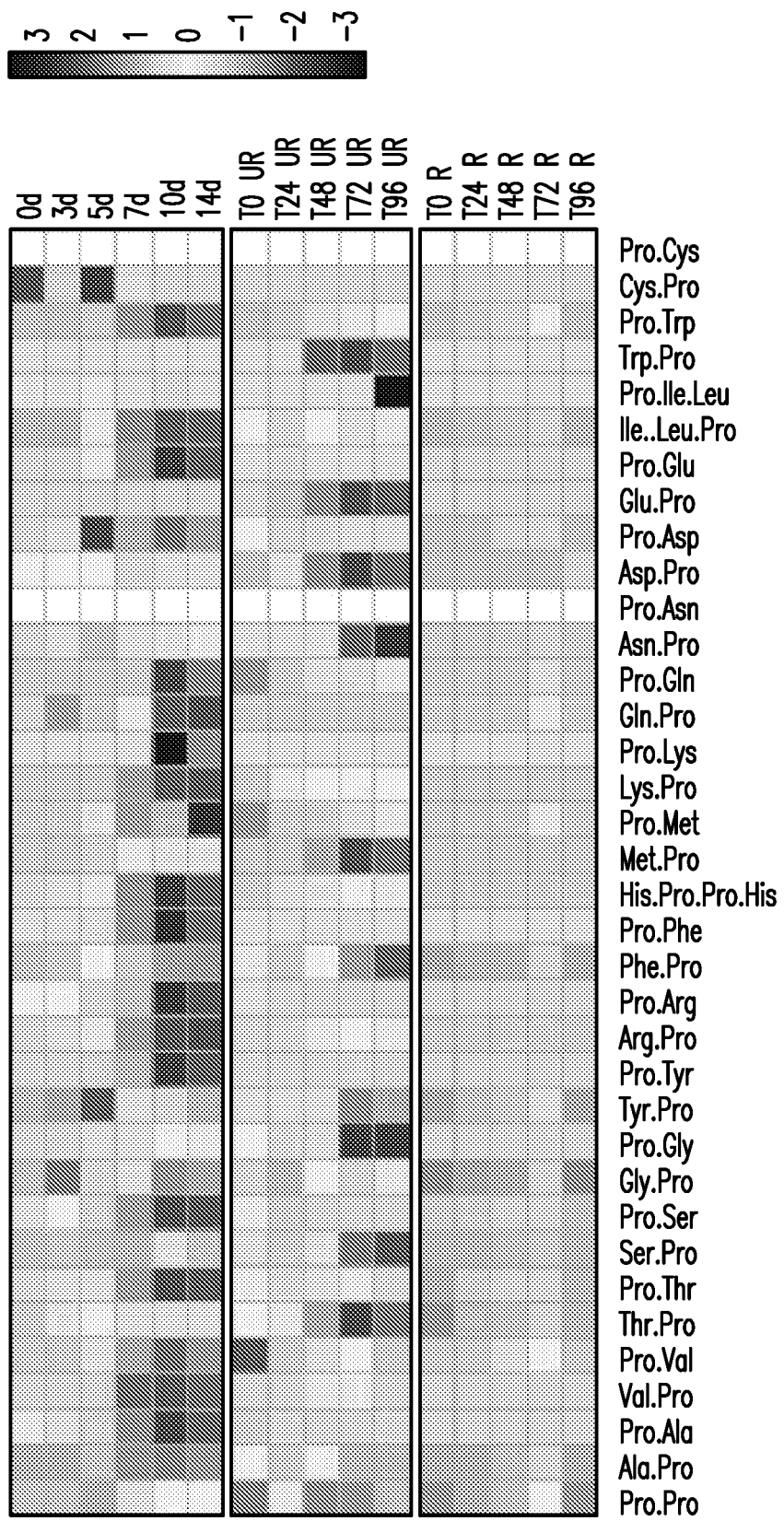
FIG. 7A depicts the concentrations of various prolyl peptides in cocoa samples.
Figure 7B:
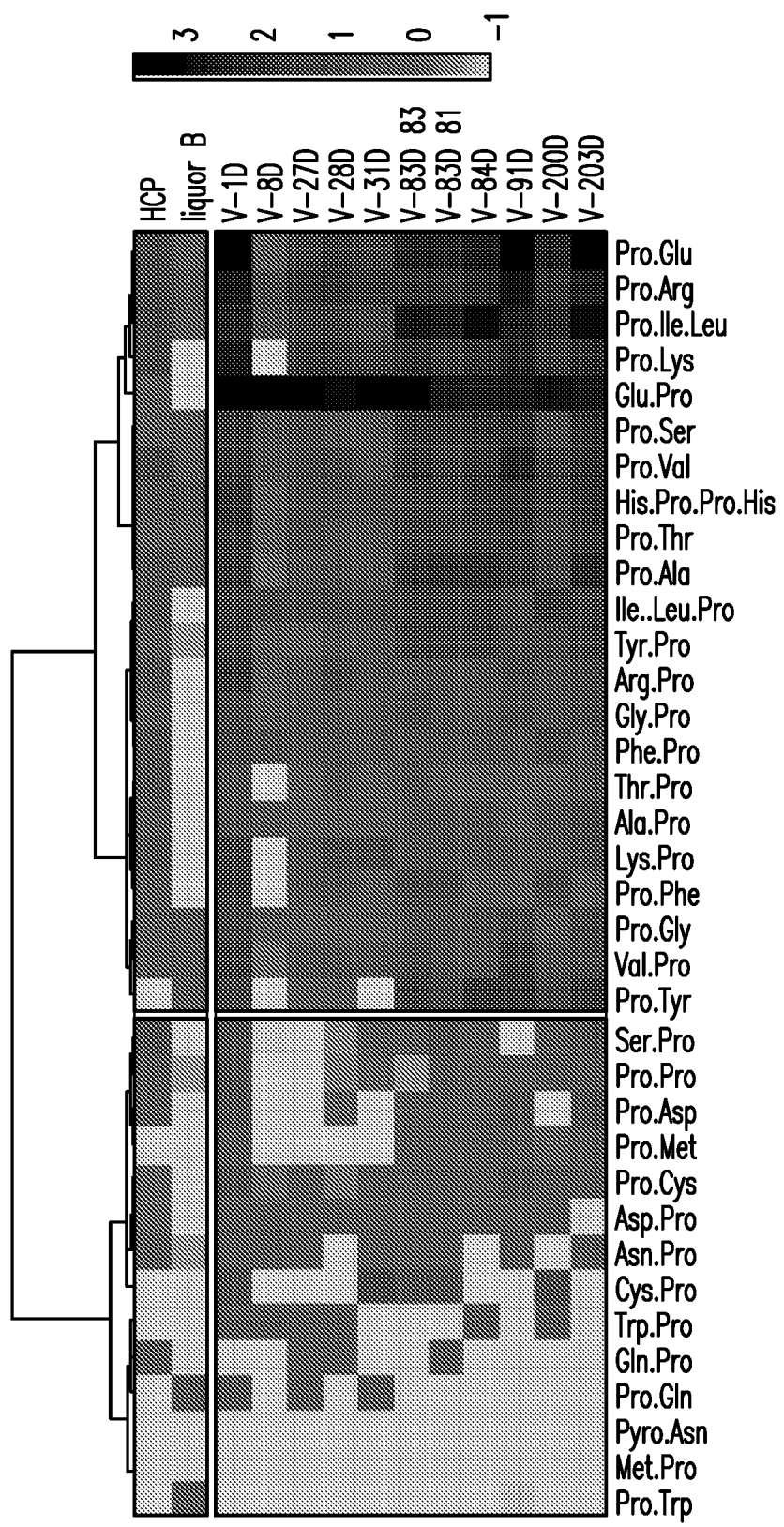
FIG. 7B depicts the concentrations of various prolyl peptides in HVP samples.

Prolyl peptides were also identified in hydrolyzed vegetable proteins (HVP). FIG. 6 shows the concentrations of prolyl peptides in HVP samples compared to cocoa samples. The sample type of each sample ID is shown in Table 3 below. The concentrations of prolyl peptides in HVP samples are much higher than in cocoa samples. The highest concentrations were present in wheat samples (V-91), whereas the lowest concentrations were present in 3 soy samples (V-27, V-28 and V-31). Concentrations of various prolyl peptides in cocoa samples and HVP samples are shown in FIGS. 7A and 7B, respectively.

TABLE 3

| Sample ID | Sample type |
|---|---|
| V-1D | soy and wheat |
| V-8D | yeast |
| V-27D | soy |
| V-28D | soy |
| V-31D | soy |
| V-83D-83 | corn |
| V-83D-81 | corn |
| V-84D | corn |
| V-91D | wheat |
| V-200D | corn, soy and wheat |
| V-203D | corn, soy and wheat |

Sensory evaluation of prolyl peptides was first conducted in model broth via duo-trio tests (pre-tests). Peptides having a positive taste modulating activity were highlighted in FIG. 8. Threshold concentrations of those peptides were then determined in model broth and in water via dilution series with duo-trio tests, the results of which are shown in Table 4.

TABLE 4

| Peptide | Threshold Concentration in Model Broth (mM) | Taste Effect | Threshold Concentration in Water (mM) | Taste Effect |
|---|---|---|---|---|
| Ala-Pro | 2.2 | Kokumi | <5 | Not taste active |
| Pro-Ala | 3.5 | Kokumi | 2.7 | Bitter |
| Pro-Ser | 1.3 | Kokumi | <5 | Not taste active |
| Ser-Pro | 0.65 | Kokumi | 3.8 | Bitter |
| Pro-Val | 1.9 | Salt enhancing | <5 | Not taste active |
| Val-Pro | 0.8 | Salt enhancing | <5 | Not taste active |
| Arg-Pro | 0.5 | Salt enhancing | 3.5 | Bitter |
| Pro-Pro | <5 | No modulation | NA | Not taste active |
| Pro-Lys | 2 | More complex | <3 | Not taste active |
| Lys-Pro | 1.2 | Salt enhancing | 2.1 | Slightly bitter |
| Pro-Gln | <5 | No modulation | NA | Not taste active |
| Pro-Glu | 0.8 | Umami enhancing | <5 | Not taste active |
| Pro-Pro | 1 | Umami enhancing | 3.8 | Bitter |

Figure 9:
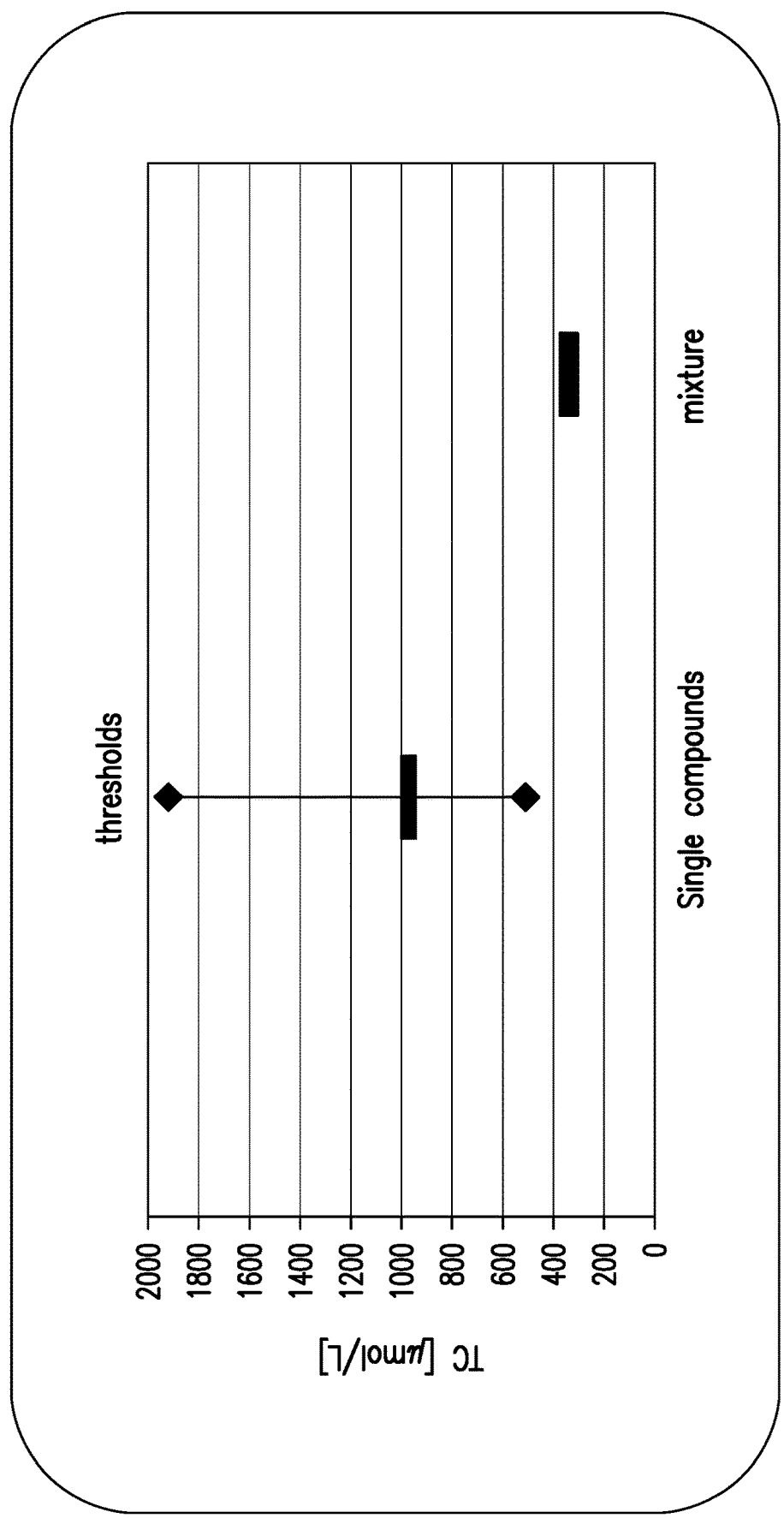
FIG. 9 depicts the threshold concentration (TC) of a mixture of prolyl peptides (Pro-Pro, Pro-Glu, Pro-Val, Ser-Pro and Arg-Pro in an equal amount) and the average TC of the individual peptides thereof.

Sensory evaluation of a mixture of prolyl peptides (Pro-Pro, Pro-Glu, Pro-Val, Ser-Pro and Arg-Pro in an equal amount) was also conducted. The taste effect of the mixture was an enhanced umami taste and an enhanced kokumi taste. FIG. 9 shows that the threshold concentration of the mixture (330 μM) was much lower than the threshold concentration of each individual peptide, which ranged from 500 μM to 1900 μM. As the theoretical threshold concentration of the mixture (without synergy) should be an average of the threshold concentrations of the individual peptides (990 μM), the mixture of taste modulating prolyl dipeptides demonstrated a synergistic effect.

Example 4—Identification of Pyroglutamyl Dipeptides as Taste Modulators

Figure 10A:
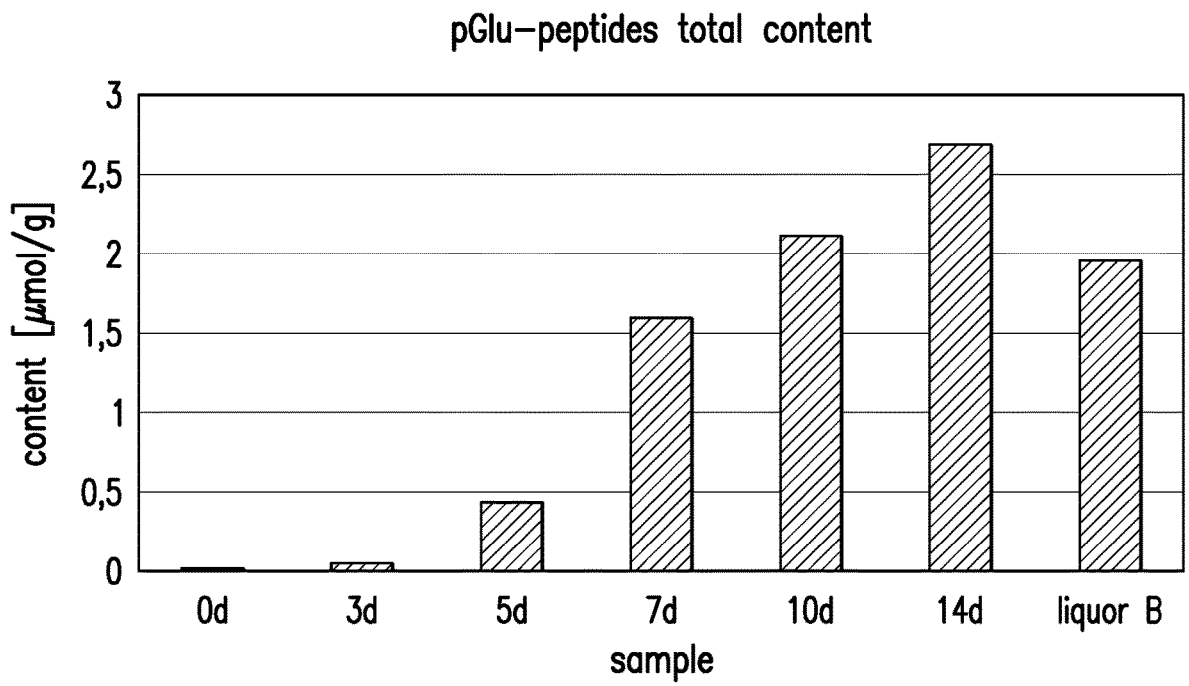
FIG. 10A depicts that pGlu-peptide levels increased with time of fermentation, and that Liquor B contained a high level of pGlu-dipeptides.
Figure 10B:
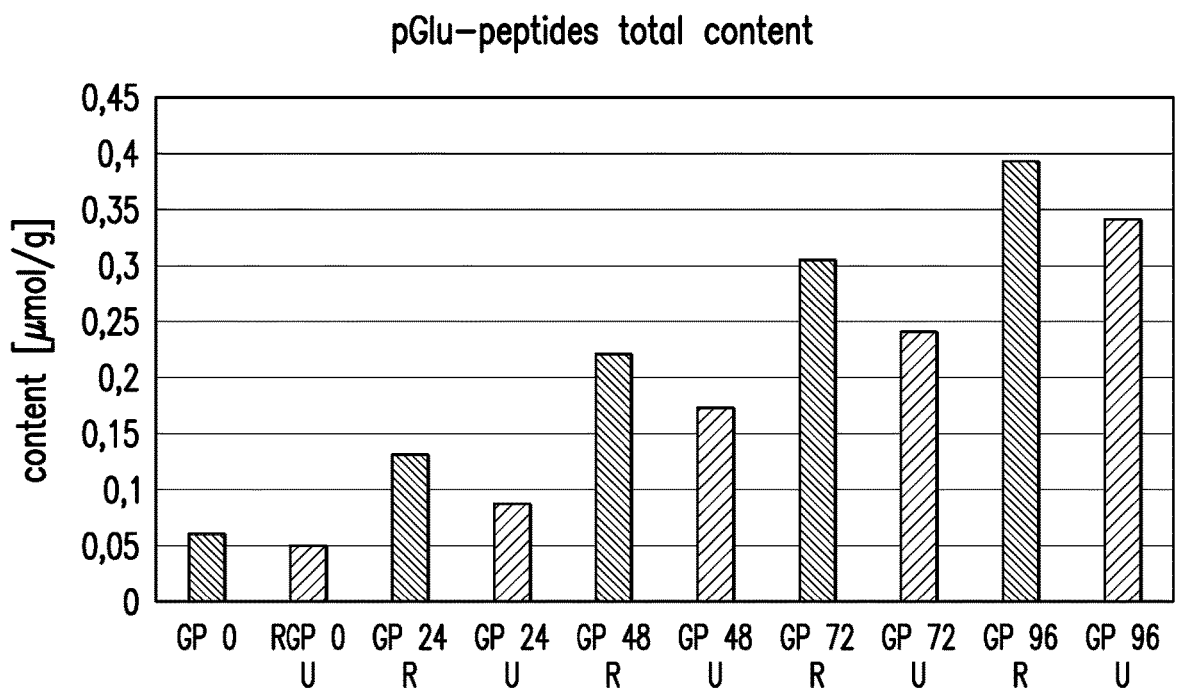
FIG. 10B depicts that pGlu-peptide levels increased with time of germination, and roasted samples contain a higher concentration. The numbers at the x-axis indicate hours of germination process. R: roasted; U: unroasted.

In addition to the various peptides disclosed in Examples 2 and 3, all pGlu-dipeptides were identified in cocoa samples described above except from pGlu-Cys. FIG. 10A shows that pGlu-peptide levels increased with time of fermentation, and that Liquor B contained a high level of pGlu-dipeptides. FIG. 10B shows that pGlu-peptide levels increased with time of germination, and roasted samples contain a higher concentration.

Figure 11:
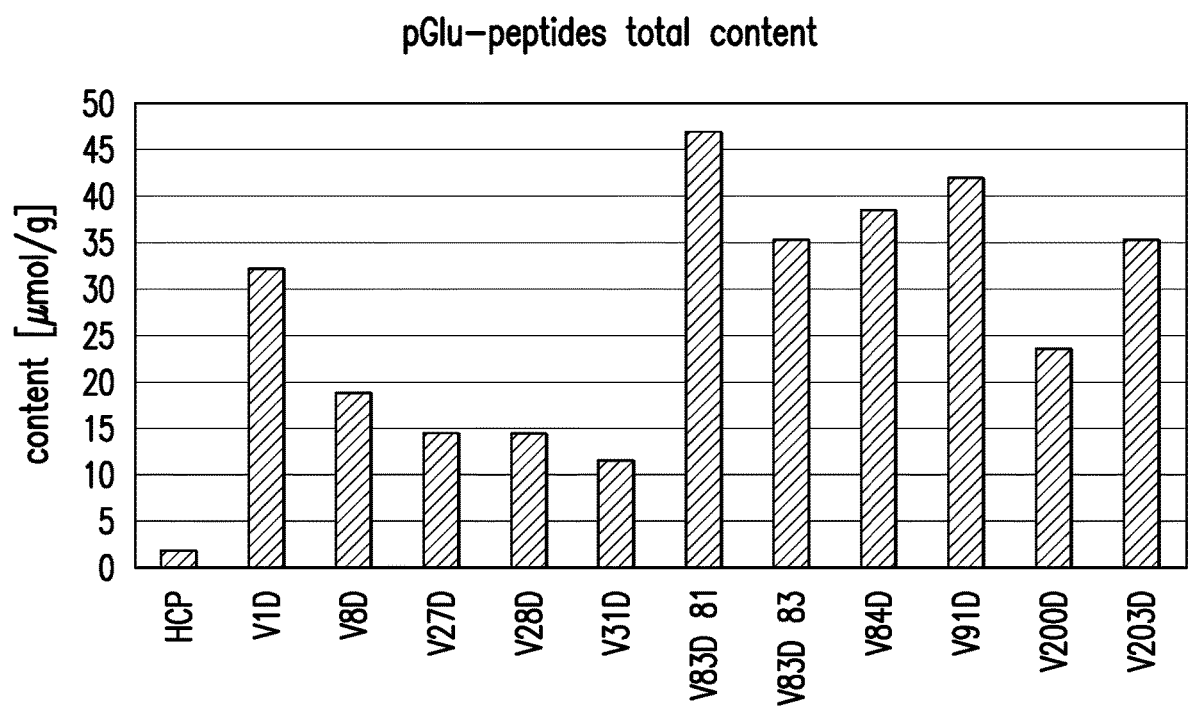
FIG. 11 depicts the concentrations of prolyl peptides in various HVP samples compared to cocoa samples (HCP).

Furthermore, pGlu-dipeptides were identified in hydrolyzed vegetable proteins (HVP). FIG. 11 shows the concentrations of prolyl peptides in HVP samples compared to cocoa samples (e.g., HCP). The sample type of each sample ID is shown in Table 3 below. The concentrations of prolylpetides in HVP samples are much higher than in cocoa samples. The highest concentrations were present in corn samples (V-83 and V-84), wheat samples (V-91) and the mixture samples of soy, wheat and/or corn (V-1 and V-203).

Sensory evaluation of pGlu-dipeptides was conducted and threshold concentrations were determined in model broth and in water. The results of representative peptides are shown in Table 5.

TABLE 5

| pGlu-X | Threshold Concentration in Model Broth (mM) | Taste Effect | Threshold Concentration in Water (mM) | Taste Effect |
|---|---|---|---|---|
| Val | 1.8 | Kokumi | 3.3 | Bitter |
| Ala | 2.7 | Complex | 2.7 | Bitter |
| Gln | 0.35 | Umami enhancing | <1 | Not taste active |
| Phe | 1.3 | Umami enhancing | | |
| Glu | 0.32 | Salt enhancing | <2.5 | Not taste active |
| Ser | 0.86 | Umami enhancing | <2.5 | Not taste active |
| Pro | 0.3 | Umami enhancing | <2.5 | Not taste active |
| Arg | 0.55 | Umami enhancing | 0.94 | Bitter |
| Leu | <2.5 | No modulation | | |
| Lys | <2.5 | No modulation | 1 | Astringent, slightly bitter |

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

What is claimed is:

1. A method of increasing a saltiness intensity in a food product comprising admixing the food product with a flavor composition comprising at least two peptides
selected from the group consisting of proline-valine (Pro-Val), valine-proline (Val-Pro), arginine-proline (Arg-Pro), proline-lysine (Pro-Lys), lysine-proline (Lys-Pro),
wherein the flavor composition peptide is present at a concentration of from about 0.1 ppb to about 1000 ppb in the admixture.

2. A method of reducing the amount of sodium chloride in a food product comprising admixing the food product with a flavor composition comprising at least two peptides
selected from the group consisting of proline-valine (Pro-Val), valine-proline (Val-Pro), arginine-proline (Arg-Pro), proline-lysine (Pro-Lys), lysine-proline (Lys-Pro),
wherein the flavor composition peptide is present at a concentration of from about 0.1 to about 1000 ppb in the admixture.

3. A method of increasing an umami intensity in a food product
comprising admixing the food product with a flavor composition comprising at least two peptides
selected from the group consisting of proline-proline (Pro-Pro), proline-glutamate (Pro-Glu), proline-valine (Pro-Val), serine-proline (Ser-Pro), arginine-proline (Arg-Pro),
wherein the flavor composition peptide is present at a concentration of from about 0.1 to about 1000 ppt.

4. The method of claim 3, wherein the flavor composition comprises proline-proline (Pro-Pro), proline-glutamate (Pro-Glu), proline-valine (Pro-Val), serine-proline (Ser-Pro), and arginine-proline (Arg-Pro).

5. The method of claim 4, wherein the peptides are present in an equal amount in the flavor composition.

6. A method of increasing a kokumi intensity in a food product comprising admixing the food product with a flavor composition comprising at least two peptides
selected from the group consisting of alanine-proline (Ala-Pro), proline-alanine (Pro-Ala), proline-serine (Pro-Ser), serine-proline (Ser-Pro), proline-proline (Pro-Pro), proline-glutamate (Pro-Glu), proline-valine (Pro-val), arginine-proline (Arg-Pro),
wherein the flavor composition peptide is present at a concentration of from about 0.1 to about 1000 ppt.

7. The method of claim 6, wherein the mixture of peptides comprises proline-proline (Pro-Pro), proline-glutamate (Pro-Glu), proline-valine (Pro-Val), serine-proline (Ser-Pro), and arginine-proline (Arg-Pro).

8. The method of claim 7, wherein the peptides are present in an equal amount in the flavor composition.

* * * * *